United States Patent
Adli et al.

(10) Patent No.: US 8,574,832 B2
(45) Date of Patent: Nov. 5, 2013

(54) METHODS FOR PREPARING SEQUENCING LIBRARIES

(75) Inventors: Mazhar Adli, Malden, MA (US); Bradley E. Bernstein, Cambridge, MA (US); Tarjei S. Mikkelsen, Cambridge, MA (US)

(73) Assignees: Massachusetts Institute of Technology, Cambridge, MA (US); The General Hospitall Corporation, Boston, MA (US)

( * ) Notice: Subject to any disclaimer, the term of this patent is extended or adjusted under 35 U.S.C. 154(b) by 370 days.

(21) Appl. No.: 12/699,508

(22) Filed: Feb. 3, 2010

(65) Prior Publication Data
US 2011/0189677 A1 Aug. 4, 2011

(51) Int. Cl.
C12Q 1/68 (2006.01)
C12P 19/34 (2006.01)
C07H 21/02 (2006.01)
C07H 21/04 (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,350 A | 2/1976 | Kronick et al. | 250/365 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 4,683,195 A | 7/1987 | Mullis et al. | 435/6.11 |
| 4,683,202 A | 7/1987 | Mullis | 435/91.2 |
| 4,981,785 A | 1/1991 | Nayak | 435/7.94 |
| 5,358,691 A | 10/1994 | Clark et al. | 422/64 |
| 5,538,848 A | 7/1996 | Livak et al. | 435/6.16 |
| 5,599,677 A | 2/1997 | Dowell et al. | 435/7.4 |
| 5,639,606 A | 6/1997 | Willey | 435/6.12 |
| 5,643,765 A | 7/1997 | Willey | 435/6.12 |
| 5,672,480 A | 9/1997 | Dowell et al. | 435/7.4 |
| 5,731,171 A * | 3/1998 | Bohlander | 435/91.2 |
| 5,846,717 A | 12/1998 | Brow et al. | 435/6.18 |
| 5,876,978 A | 3/1999 | Willey et al. | 435/91.2 |
| 5,885,530 A | 3/1999 | Babson et al. | 422/65 |

(Continued)

FOREIGN PATENT DOCUMENTS

WO WO/89/09283 10/1989
WO WO/93/23564 11/1993

(Continued)

OTHER PUBLICATIONS

Anand, R. et al., Nucl. acids res., vol. 18, pp. 1951-1956 (1990).*

(Continued)

Primary Examiner — Teresa E Strzelecka
(74) Attorney, Agent, or Firm — Medlen & Carroll, LLP

(57) ABSTRACT

Improvements in chromatin immunoprecipitation-high throughput sequencing techniques has allowed the creation of chromatin maps from limited biological sample sizes that cannot be evaluated using conventional chromatin immunoprecipitation-sequencing protocols. For example, a modified universal primer is utilized that incorporates restriction enzymes into chromatin immunoprecipitation fragments before amplification. The improved method allows the sample sizes to be several orders of magnitude less than that required for standard ChIP-Seq techniques.

7 Claims, 14 Drawing Sheets

(56) References Cited

U.S. PATENT DOCUMENTS

| | | | | |
|---|---|---|---|---|
| 5,985,557 | A | 11/1999 | Prudent et al. | 435/6.1 |
| 5,994,069 | A | 11/1999 | Hall et al. | 435/6.18 |
| 6,001,567 | A | 12/1999 | Brow et al. | 435/5 |
| 6,090,543 | A | 7/2000 | Prudent et al. | 435/6.18 |
| 6,159,750 | A | 12/2000 | Edmonds | 436/537 |
| 6,586,237 | B1 * | 7/2003 | Yesland | 435/320.1 |
| 7,252,968 | B2 | 8/2007 | Jenuwein et al. | 435/69.1 |
| 7,527,970 | B2 | 5/2009 | Zhao | 435/325 |
| 7,635,561 | B2 | 12/2009 | Giordano | 435/6.14 |
| 2004/0115815 | A1 * | 6/2004 | Li et al. | 435/456 |

FOREIGN PATENT DOCUMENTS

| | | |
|---|---|---|
| WO | WO/98/13523 | 4/1998 |
| WO | WO/98/28440 | 7/1998 |
| WO | WO/00/43540 | 7/2000 |

OTHER PUBLICATIONS

New England Biolabs listing of restriction enzymes generating single-nucleotide overhangs (downloaded from www.neb.com/nebecomm/EnzymeFinderSearchByEnd.asp?.. Jul. 3, 2012).*

Engler, C. et al., PLOS One, vol. 3, e3647, pp. 1-7 (2008).*

Acevedo, L. G. et al. (2007) Genome-scale ChIP-chip analysis using 10,000 human cells, *BioTechniques* 43(6), 791-797.

Akan, P. et al. (2009) A Histone Map of Human Chromosome 20q13.12, *PLoS One* 4(2), e4479.

Assland, R. and Stewart, F. (1995) The chromo shadow domain, a second chromo domain in heterochromatin-binding protein 1, HP1, *Nucleic Acids Res.* 23(16), 3168-3173.

Attema, J. L. et al. (2007) Epigenetic characterization of hematopoietic stem cell differentiation using miniChIP and bisulfite sequencing analysis, *Proc. Natl. Acad. Sci. U. S. A.* 104(30), 12371-12376.

Azuara, V. et al. (2006) Chromatin signatures of pluripotent cell lines, *Nat. Cell Biol.* 8(5), 532-538.

Ball, L. J. et al. (1997) Structure of the chromatin binding (chromo) domain from mouse modifier protein 1, *EMBO J.* 16(9), 2473-2481.

Ballestar, E. (2010) Epigenetics Lessons from Twins: Prospects for Autoimmune Disease, *Clin. Rev. Allergy Immunol.* 39(1), 30-41.

Barski, A. et al. (2007) High-Resolution Profiling of Histone Methylations in the Human Genome, *Cell* 129(4), 823-837.

Bernstein, B. E. et al. (2005) Genomic Maps and Comparative Analysis of Histone Modifications in Human and Mouse, *Cell* 120(2), 169-181.

Bernstein, B. E. et al. (2006) A Bivalent Chromatin Structure Marks Key Developmental Genes in Embryonic Stem Cells, *Cell* 125(2), 315-326.

Bottardi, S. et al. (2007) Lineage-Specific Transcription Factors in Multipotent Hematopoietic Progenitors: A Little Bit Goes a Long Way, *Cell Cycle* 6(9), 1035-1039.

Chambers, S. M. et al. (2007) Hematopoietic Fingerprints: An Expression Database of Stem Cells and Their Progeny, *Cell Stem Cell* 1(5), 578-591.

Cui, K. et al. (2009) Chromatin Signatures in Multipotent Human Hematopoietic Stem Cells Indicate the Fate of Bivalent Genes during Differentiation, *Cell Stem Cell* 4(1), 80-93.

Dahl, J. A. and Collas, P. (2007) $Q^2ChIP$, a Quick and Quantitative Chromatin Immunoprecipitation Assay, Unravels Epigenetic Dynamics of Developmentally Regulated Genes in Human Carcinoma Cells, *Stem Cells* 25(4), 1037-1046.

Delcuve, G. P. et al. (2009) Epigenetic control, *J. Cell. Physiol.* 219(2), 243-250.

Forsberg, E. C. et al. (2005) Differential Expression of Novel Potential Regulators in Hematopoietic Stem Cells, *PLoS Genet.* 1(3), e28.

Gorelik, G. and Richardson, B. (2009) Aberrant T cell ERK pathway signaling and chromatin structure in lupus, *Autoimmun. Rev.* 8(3), 196-198.

Jenuwein, T. et al. (1998) SET domain proteins modulate chromatin domains in eu- and heterochromatin, *Cell. Mol. Life Sci.* 54(1), 80-93.

Köhler, G. and Milstein, C. (1975) Continuous cultures of fused cells secreting antibody of predefined specificity, *Nature* 256(5517), 495-497.

Ku, M. et al. (2008) Genomewide Analysis of PRC1 and PRC2 Occupancy Identifies Two Classes of Bivalent Domains, *PLoS Genet.* 4(10), e1000242.

Maniatis, T. et al. (1987) Regulation of inducible and tissue-specific gene expression, *Science* 236(4806), 1237-1245.

Mikkelsen, T. S. et al. (2007) Genome-wide maps of chromatin state in pluripotent and lineage-committed cells, *Nature* 448(7153), 553-560.

Morrison, S. J. and Weissman, I. L. (1994) The long-term repopulating subset of hematopoietic stem cells is deterministic and isolatable by phenotype, *Immunity* 1(8), 661-673.

Nicholas, A. P. et al. (2008) Striatal histone modifications in models of levodopa-induced dyskinesia, *J. Neurochem.* 106(1), 486-494.

O'Neill, L. P. and Turner, B. M. (1996) Immunoprecipitation of chromatin, *Methods Enzymol.* 274, 189-197.

Ogawa, M. (1993) Differentiation and proliferation of hematopoietic stem cells, *Blood* 81(11), 2844-2853.

Orford, K. et al. (2008) Differential H3K4 Methylation Identifies Developmentally Poised Hematopoietic Genes, *Dev. Cell* 14(5), 798-809.

Orkin, S. H. and Zon, L. I. (2008) Hematopoiesis: An Evolving Paradigm for Stem Cell Biology, *Cell* 132(4), 631-644.

Park, P. J. (2009) ChIP-seq: advantages and challenges of a maturing technology, *Nat. Rev. Genet.* 10(10), 669-680.

Pedrosa, E. et al. (2009) Survey of Schizophrenia and Bipolar Disorder Candidate Genes using Chromatin Immunoprecipitation and Tiled Microarrays (ChIP-chip), *J. Neurogenet.* 23(3), 341-352.

Platero, J. S. et al. (1995) Functional analysis of the chromo domain of HP1, *EMBO (Eur. Mol. Biol. Organ.) J.* 14(16), 3977-3986.

Schwartz, Y. B. and Pirrotta, V. (2007) Polycomb silencing mechanisms and the management of genomic programmes, *Nat. Rev. Genet.* 8(1), 9-22.

Tothova, Z. et al. (2007) FoxOs Are Critical Mediators of Hematopoietic Stem Cell Resistance to Physiologic Oxidative Stress, *Cell* 128(2), 325-339.

Uchida, N. et al. (1994) Rapid and sustained hematopoietic recovery in lethally irradiated mice transplanted with purified Thy-1.1lo Lin-Sca-1+ hematopoietic stem cells, *Blood* 83(12), 3758-3779.

Varnum-Finney, B. et al. (2008) Notch target Hes5 ensures appropriate Notch induced T- versus B-cell choices in the thymus, *Blood* 111(5), 2615-2620.

Verlaan, D. J. et al. (2009) Allele-Specific Chromatin Remodeling in the ZPBP2/GSDNB/ORMDL3 Locus Associated with the Risk of Asthma and Autoimmune Disease, *Am. J. Hum. Genet.* 85(3), 377-393.

Visel, A. et al. (2009) ChIP-seq accurately predicts tissue-specific activity of enhancers, *Nature* 457(7231), 854-858.

Wei, G. et al. (2009) Global Mapping of H3K4me3 and H3K27me3 Reveals Specificity and Plasticity in Lineage Fate Determination of Differentiating CD4+ T Cells, *Immunity* 30(1), 155-167.

Weishaupt, H. et al. (2010) Epigenetic chromatin states uniquely define the developmental plasticity of murine hematopoietic stem cells, *Blood* 115(2), 247-256.

Zhu, W. et al. (2010) Thrombin induces endothelial arginase through AP-1 activation, *Am. J. Physiol. Cell Physiol.* 298(4), C952-C960.

Anderson, M. L. M. and Young, B. D. (1985) Quantitative Filter Hybridization, in Nucleic Acid Hybridisation: A Practical Approach (Hames, B. D., and Higgins, S. J., Eds.), pp. 73-111, Oxford University Press, USA.

Collas, P. (2009) The State-of-the-Art of Chromatin Immunoprecipitation: Chromatin Immunoprecipitation Assays, (Collas, P., Ed.), pp. 1-25, Humana Press.

Koonin, E. V. et al. (1995) The chromo superfamily: new members, duplication of the chromo domain and possible role in delivering transcription regulators to chromatin, *Nucleic Acids Res.* 23(21), 4229-4233.

(56) References Cited

OTHER PUBLICATIONS

O'Neill, L. P. et al. (2006) Epigenetic characterization of the early embryo with a chromatin immunoprecipitation protocol applicable to small cell populations, Nat. Genet. 38(7), 835-841.

Sambrook, J. et al., (Eds.) (1989) Molecular Cloning: A Laboratory Manual, 2nd ed., Cold Spring Harbor Laboratory Press, New York.
Dieffenbach, C. W. and Dveksler, G. S. (1995) PCR Primer, A Laboratory Manual, Cold Spring Harbor Laboratory Press, Plainview, N.Y.
US 5,962,233, 10/1999, Livak et al. (withdrawn)

* cited by examiner

A

BciVI

*Recognition Sequence*

...GTATCCNNNNNN↓N...
...CATAGGNNNNN↑NN...

*After cut*

...GTATCCNNNNNN  N...
...CATAGGNNNNN  NN...

B

BfuI

*Recognition Sequence*

...GTATCCNNNNNN↓N...
...CATAGGNNNNN↑NN...

*After cut*

...GTATCCNNNNNN  N...
...CATAGGNNNNN  NN...

METHODS FOR PREPARING SEQUENCING LIBRARIES

STATEMENT OF GOVERNMENTAL SUPPORT

This invention was made with government support under contract number 1R01HG004401-01 awarded by National Human Genome Research Institute. The government has certain rights in the invention.

FIELD OF THE INVENTION

The present invention is related to the field of genomics. In particular, the invention is related to genome-wide mapping and high throughput sequencing from a biological sample having a low number of cells. In some cases, a chromatin map identifying gene locations may be determined when using between approximately 1,000-100,000 cells. For example, histone-DNA modifications have been mapped in hematopoetic stem cells using a biological sample containing approximately 20,000 cells.

BACKGROUND

Sequencing platforms (i.e., for example, Illumina GA, ABI SOLiD, Helicoscope) are capable of acquiring vast numbers of sequencing reads and high base coverage at greatly reduced costs. This capacity and cost-effectiveness has opened up new markets and applications for sequencing in the area of functional genomics; that is, the characterization of protein-DNA interactions, chromatin state, copy number variations and RNA expression.

One step in these functional genomic applications is the preparation of DNA libraries suitable for sequencing. Standard library preparation procedures require 0.1-1 µg DNA at the start. This severely limits that applicability of the technologies to experiments in which large amounts of starting sample is available (e.g., millions of cells). As an example, many cell populations and tissues are not amenable to chromatin state analysis due to insufficient cell numbers.

What is needed in the art is a method for preparing DNA sequencing libraries using a source material quantity substantially less than 0.1 µg (i.e., for example, picograms).

SUMMARY OF THE INVENTION

The present invention is related to the field of genomics. In particular, the invention is related to genome-wide mapping from a biological sample having a low number of cells. In some cases, a chromatin map identifying gene locations may be determined when using between approximately 1,000-100,000 cells. For example, histone-DNA modifications have been mapped in hematopoetic stem cells using a biological sample containing approximately 25,000 cells.

In one embodiment, the present invention contemplates a method for generating a sequencing library from trace quantities of genomic deoxyribonucleic acid (DNA). In one embodiment, the method comprises extending, amplifying, and digesting the trace DNA quantities. In one embodiment, the trace DNA comprises approximately between 0.1-1,000 picograms.

In one embodiment, the present invention contemplates a composition comprising an amplified DNA fragment comprising a random nucleic acid sequence, a 3' restriction site, and a 5' restriction site, wherein the 3' and 5' restriction sites are identical. In one embodiment, the amplified DNA fragment is an amplified ChIP DNA fragment. In one embodiment, the amplified DNA fragment is an amplified restriction DNA fragment. In one embodiment, the amplified DNA fragment is a sonicated DNA fragment. In one embodiment, the random nucleic acid sequence comprises between approximately eight to eleven nucleic acids. In one embodiment, the random nucleic acid sequence comprises nine nucleic acids. In one embodiment, the composition further comprises a restriction enzyme having specific affinity for the 3' restriction site and a 5' restriction site. In one embodiment, the composition further comprises a universal primer sequence ranging between approximately four-thirteen nucleic acids.

In one embodiment, the present invention contemplates a complex comprising: a) a primer comprising a restriction site, at least one universal primer nucleic acid sequence, and a random nucleic acid sequence; b) a DNA fragment comprising at least partial complementarity to said universal primer; and c) a DNA polymerase. In one embodiment, the DNA fragment is a ChIP DNA fragment. In one embodiment, the DNA fragment is a restriction fragment. In one embodiment, the DNA fragment is a sonication fragment. In one embodiment, the random nucleic acid sequence comprises between approximately eight to eleven nucleic acid residues. In one embodiment, the random nucleic acid sequence comprises nine nucleic acid residues. In one embodiment, the primer is a hairpin primer. In one embodiment, the hairpin primer comprises a closed loop, a duplex region, and an open loop. In one embodiment, the polymerase has no 3'→5' exonuclease activity. In one embodiment, the polymerase comprises strand displacement activity. In one embodiment, the universal primer nucleic acid sequence comprises between approximately four-thirteen nucleic acids. In one embodiment, the universal primer nucleic acid sequence comprises a terminal "T" nucleotide. In one embodiment, the restriction site comprises a BciVI restriction site. In one embodiment, the restriction site comprises a BfuI restriction site. In one embodiment, the restriction site comprises a 3' site selected from the group consisting of those listed in Table 1A. In one embodiment, the restriction site comprises a 5' site selected from the group consisting of those listed in Table 1B.

In one embodiment, the present invention contemplates a method comprising: a) providing; i) a plurality of genomic DNA fragments derived from a biological sample comprising less than 50,000 cells; ii) a first primer capable of creating a first extension product of one or more of said DNA fragments, wherein said primer comprises at least one restriction enzyme binding site, at least one universal primer sequence ranging between four and thirteen nucleotides in length, and at least one random nucleotide sequence of at least eight nucleotides in length; iii) a second primer capable of amplifying said first extension product so as to create a second extension product; iv) a restriction enzyme capable of cleaving said second extension product based on said restriction enzyme binding site; and v) a polymerase; b) extending said DNA fragment with said first primer and said polymerase so as to create a first extension product; c) amplifying said first extension product with said second primer and said polymerase so as to create a second extension product; d) cleaving said second extension product between said at least one universal primer sequence and said random sequence with a restriction enzyme, thereby creating a cleavage product comprising an overhang. In one embodiment, the method further comprises step e) attaching a sequencing adapter to said cleavage via the overhang. In one embodiment, the genomic DNA fragments comprise genomic DNA ChIP fragments. In one embodiment, the genomic DNA fragments comprise genomic DNA restriction fragments. In one embodiment, the genomic DNA fragments comprise genomic DNA sonication fragments. In one embodiment, the random nucleotide sequence comprises between approximately eight to eleven nucleic acids. In one embodiment, the random nucleotide sequence comprises nine nucleic acids. In one embodiment, the first primer comprises a hairpin primer. In one embodiment, the hairpin primer comprises a closed loop, a duplex region, and an open loop. In one embodiment, the polymerase has no 3'→5' exonuclease activity. In one embodiment, the polymerase comprises strand displacement activity. In one embodiment, the sequencing adapter comprises a Solexa adapter. In one embodiment, the sequencing adapter comprises an Illumina adapter.

In one embodiment, the present invention contemplates a method comprising: a) providing; i) a DNA fragment derived from a biological sample comprising less than 50,000 cells; ii) a first polymerase capable of creating an extended DNA fragment, wherein the extended DNA fragment comprises at least one restriction enzyme binding site, at least one universal primer sequence ranging between four and thirteen nucleic acids, and at least one random nucleotide sequence; iii) a second polymerase capable of amplifying the extended DNA fragment; iv) a restriction enzyme capable of cleaving the at least one random nucleotide sequence; and v) a solid substrate capable of attaching the amplified DNA fragment; b) extending the DNA fragment with the first polymerase; c) amplifying the extended DNA fragment with the second polymerase; d) cleaving the random nucleotide with a restriction enzyme, thereby creating a fragment amplicon. In one embodiment, the method further comprises step e) attaching the fragment amplicons to the solid substrate. In one embodiment, the extended DNA fragment comprises a 5' restriction site and a 3' restriction site. In one embodiment, the 5' restriction site and 3' restriction site are identical. In one embodiment, the DNA fragment comprises a ChIP DNA fragment. In one embodiment, the DNA fragment comprises a restriction DNA fragment. In one embodiment, the DNA fragment comprises a sonication DNA fragment. In one embodiment, the random nucleotide sequence comprises between approximately eight to eleven nucleic acid residues. In one embodiment, the random nucleotide sequence comprises nine nucleic acid residues. In one embodiment, the at least one universal primer sequence comprises a terminal "T" nucleic acid. In one embodiment, the restriction enzyme cleaves the fragment amplicon between the random nucleotide sequence and the at least one universal primer sequence, wherein a terminal "T" nucleic acid overhang is created. In one embodiment, the amplicons comprise at least one sticky end comprising an "A" nucleic acid overhang. In one embodiment, the amplicons comprise at least one blunt end. In one embodiment, the method further comprises attaching a sequencing adapter to the amplicons. In one embodiment, the sequencing adapter comprises a Solexa sequencing adapter. In one embodiment, the sequencing adapter comprises an Illumina sequencing adapter. In one embodiment, the method further comprises sequencing of the amplicons. In one embodiment, the method further comprises identifying at least one genomic modification. In one embodiment, the at least one genomic modification is a histone modification. In one embodiment, the method further comprises compiling the at least one histone modifications wherein a chromatin map is created.

In one embodiment, the present invention contemplates a method comprising: a) providing: i) a first chromatin map derived from a small population of normal biological cells (i.e., for example, between approximately 1,000 to 100,000 cells); and ii) a second chromatin map derived from a small population of biological cells comprising a disease; and b) comparing the first chromatin map to a second chromatin map wherein the disease is diagnosed. In one embodiment, the comparing identifies a differential histone modification pattern. In one embodiment, the disease comprises a cancer. In one embodiment, the cancer comprises a malignant cancer. In one embodiment, the disease comprises a neurological disease. In one embodiment, the neurological disease comprises Alzhemier's disease. In one embodiment, the neurological disease comprises a behavioral disorder. In one embodiment, the neurological disease comprises Parkinson's disease. In one embodiment, the disease comprises a cardiovascular disease. In one embodiment, the cardiovascular disease comprises an arterial thrombosis. In one embodiment, the disease comprises an autoimmune disease. In one embodiment, the autoimmune disease comprises diabetes. In one embodiment, the autoimmune disease comprises lupus. In one embodiment, the autoimmune disease comprises Crohn's disease. In one embodiment, the autoimmune disease comprises asthma.

In one embodiment, the present invention contemplates a method comprising: a) providing; i) a first biological sample derived from a subject believed to be at risk for a medical condition, wherein the first sample comprises less than 2 nanograms of genomic DNA; ii) a second biological sample derived from a subject not believed to be at risk for the medical condition, wherein the second sample comprises less than 2 nanograms of genomic DNA; b) sequencing the DNA from the first and second biological samples to create first and second genomic modification pattern; b) detecting a difference between the first and second genomic modification patterns. In one embodiment, the method further comprises diagnosing the medical condition based upon the detected difference between the first and second genomic modification patterns. In one embodiment, the first and second genomic modification patterns comprise histone-DNA modifications.

In one embodiment, the present invention contemplates a method comprising: a) providing; i) a first biological sample derived from a subject exhibiting at least one symptom of a medical condition, wherein the first sample comprises less than 2 nanograms of genomic DNA; ii) a second biological sample derived from a subject not exhibiting at least one symptom of the medical condition, wherein the second sample comprises less than 2 nanograms of genomic DNA; b) sequencing the DNA from the first and second biological samples to create first and second genomic modification patterns; b) detecting a difference between the first and second genomic modification patterns. In one embodiment, the method further comprises diagnosing the medical condition based upon the detected difference between the first and second genomic modification patterns. In one embodiment, the first and second genomic modification patterns comprise histone-DNA modifications.

In one embodiment, the present invention contemplates a method, comprising: a) providing; i) a biological sample comprising approximately between 10,000-20,000 cells, wherein the cells comprise chromatin; ii) a sonifier capable of generating soluble chromatin fragments; iii) an antibody comprising high affinity for an epitope on the chromatin fragments; iv) a solid substrate capable of binding the antibody; and v) a filter column capable of collecting the solid substrate; b) lysing the cells wherein a chromatin lysate is created; c) sonicating the chromatin lysate wherein the soluble chromatin fragments range between approximately 200-700 basepairs; c) immunoprecipitating the soluble chromatin fragments with the antibody to create an immunoprecipitate; d) attaching the immunoprecipitate to the solid substrate; e) collecting the solid substrate-immunoprecipitate on the filter column. In one embodiment, the soluble chromatin fragment comprises deoxyribonucleic acid. In one embodiment, the soluble chromatin fragment comprises ribonucleic acid. In one embodiment, the sonicating comprises a plurality of pulses. In one embodiment, the pulse is less than one second. In one embodiment, the pulse is 0.7 second. In one embodiment, the sonicating comprises a duration of less than 200 seconds. In one embodiment, the sonicating comprises a duration of less than 155 seconds. In one embodiment, the sonicating comprises a duration of less than 110 seconds. In one embodiment, the sonifier is set at less than a 75% power amplitude. In one embodiment, the sonifier is set at less than a 50% power amplitude. In one embodiment, the sonifier is set at less than a 40% power amplitude. In one embodiment, the solid substrate comprises a plurality of beads. In one embodiment, the plurality of beads comprises sepharose. In one embodiment, the sepharose is attached to Protein A. In one embodiment, the method further comprises step f) eluting the immunoprecipitate from the solid substrate. In one embodiment, the method further comprises step g) digesting the eluted immunoprecipitate with a proteinase thereby releasing the chromatin fragments comprising the epitope. In one embodiment, the method further comprising step h) extracting the epitope-containing chromatin fragment.

In one embodiment, the present invention contemplates a kit comprising: a) a first container comprising a DNA fragment, wherein said fragment comprises a random nucleic acid sequence, a 3' restriction site, and a 5' restriction site, wherein said 3' and 5' restriction sites are identical; b) a second container comprising a restriction enzyme that cleaves at the 3' restriction site and the 5' restriction site; c) a third container comprising an antibody having a high affinity for a chromatin epitope; d) a fourth container comprising enzymes capable of performing polymerase chain reaction and/or reverse transcriptase polymerase chain reaction; and e) instructional materials containing directions providing for the use of the reagents in preparing DNA fragments from small populations of cells (i.e., for example, between approximately 10,000-50,000 cells). In one embodiment, the DNA fragment is a primer. In one embodiment, the primer is a hairpin primer. In one embodiment, the instructions describe a modified chromatin immunoprecipitation method capable of generating soluble chromatin fragments having a size ranging between approximately 200-700 basepairs. In one embodiment, the instructional materials comprise written or printed materials. In one embodiment, the instructional material comprises electronic storage media.

DEFINITIONS

The term "amplified DNA fragment" as used herein, refers to any nucleic acid sequence having undergone at least one round of polymerase chain reaction amplification. The nucleic acid sequence may be derived from either genomic DNA or genomic RNA, wherein genomic RNA would be amplified by reverse transcriptase polymerase chain reaction. DNA fragments contemplated herein range between approximately 10-5,000 base pairs, preferable between approximately 100-2,500 base pairs, more preferably between approximately, 150-1,000 base pairs, and most preferably between approximately 200-700 base pairs.

The term "random nucleic acid sequence" as used herein refers to any nucleic acid sequence generated without regard to primary structure. For example, a random nucleic acid sequence may created using an automated nucleic acid synthesizer machine. Random nucleic acid sequences contemplated herein range in size between approximately 5-19 nucleic acids, preferably between approximately 8-11 nucleic acids, and more preferably 9 nucleic acids. Alternatively, the random nucleic acid sequences may be modified such that the G-C composition is enriched. For example, the relative concentrations of G and C may be increased as compared to A, T or U, such that a probability of attaching a G or C is greater than that of an A, T, or U.

The term "read length" as used herein refers to the number of accurately sequenced nucleic acid residues derived from an amplified DNA fragment. As contemplated herein, a read length may vary between approximately 16-50 nucleic acids, preferably, 25-40 nucleic acids, but most preferably 37 nucleic acids. Read length may be influenced by a number of factors including, but not limited to, the type of sequencing technique (i.e., for example, pyrosequencing, 454 sequencing, Solexa sequencing etc.), and the amplification nucleic acid complex. One type of amplification complex may include, but is not limited to, an amplified DNA fragment, a primer, and a random nucleic acid sequence. As discussed above, the random nucleic acid sequences contemplated herein may be configured to modify the read length. For example, as the length of the random nucleic acid sequence increases, the read length concomitantly decreases. Although it is not necessary to understand the mechanism of an invention, it is believed that if a random nucleic acid sequence is not long enough it will fail to bind to the DNA fragment. Alternatively, it is believed that if a random nucleic acid sequence is excessively long, a portion of the random sequence is inappropriately sequenced thereby preventing re-alignment to the genome.

The term "amplified chromatin immunoprecipitated DNA fragment" as used herein refers to an amplified DNA fragment created by the improved chromatin immunoprecipitation technique for a small cell population as described herein.

The term "amplified restriction DNA fragment" as used herein refers to an amplified DNA fragment created by digestion with restriction enzymes.

The term "amplified sonicated DNA fragment" as used herein refers to an amplified DNA fragment created by sonification.

The term "universal primer sequence" as used herein refer to any primer pair having the capability of amplifying any DNA nucleic acid sequence regardless of primary structure. For example, a universal primer pair may comprise:

```
                                            (SEQ ID NO: 13)
    forward primer: AGA GTT TGA TCC TGG CTC AG (SEQ ID NO: 14)
    reverse primer: ACG GCT ACC TTG TTA CGA CTT.
```

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific affinity" or "specific binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabelled A) in a reaction containing labeled "A" and the antibody will reduce the amount of labeled A bound to the antibody.

The term "immunologically active" defines the capability of a natural, recombinant or synthetic peptide, or any oligopeptide thereof; to induce a specific immune response in appropriate animals or cells and/or to bind with specific antibodies.

The term "epitope" or "antigenic determinant" as used herein refers to that portion of a molecule that is recognized by a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "genomic" as used herein refers to source any nuclear material related to a set of chromosomes derived from a biological cell (i.e., as opposed to a set of mitochondrial chromosomes). For example, such nuclear material may include, but is not limited to, DNA, RNA, or proteins (i.e., for example, histones).

The term "chromatin map" as used herein, refers to any display of data regarding histone modifications. For example, modifications across a genome using chromatin immunoprecipitation coupled with DNA microarrays produce high-resolution genome-wide maps of histone acetylation and methylation.

The term "histone modification pattern" as used herein refers to any recognizable changes on a chromatin map that signifies nucleosome occupancy at actively transcribed genes and/or modifications associated with gene expression. For example, both acetylation and methylation of histones are believed associated with transcriptional activity, but the former occurs predominantly at the beginning of genes whereas the latter can occur throughout transcribed regions. Most notably, specific methylation events are associated with the beginning, middle and end of actively transcribed genes.

The term "medical condition" as used herein, refers to any description of the present status of a biological organism as determined by properly trained personnel (i.e., for example, a doctor, nurse, nurse practitioner, or veterinarian). A medical condition may include, but not be limited to, healthy, diseased, or infected.

The term "healthy" or "normal" as used herein, refers to a medical condition wherein all clinical tests are within medically accepted homeostatic ranges and the patient is not in pain The term "diseased" as used herein refers to a medical condition wherein at least one clinical test is not within a medically accepted homeostatic range. For example, the clinical test may identify diseases including but not limited to, genetically predispositioned diseases (i.e., for example, cancer diseases or autoimmune diseases), infectious diseases (i.e., for example, bacterial, viral or fungal), or spontaneous and/or environmentally-induced diseases (i.e., for example, cancer diseases, cardiovascular diseases, or neurological disorders).

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "attached" as used herein, refers to any interaction between two compositions. For example, a solid substrate may be attached to a nucleic acid. Alternatively, a first molecule (i.e., for example, an amplicon) may be attached to a second molecule (i.e., for example, a sequencing adapter). Attachment may be reversible or irreversible. Such attachment includes, but is not limited to, covalent bonding, ionic bonding, Van der Waals forces or friction, and the like.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "derived from" as used herein, refers to the source of a compound or sequence. In one respect, a compound or sequence may be derived from an organism or particular species. In another respect, a compound or sequence may be derived from a larger complex or sequence.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to "apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed by a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$, of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands.

As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: *PCR Primer, a Laboratory Manual*, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence. DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., *Science* 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

Step 1: ChIP DNA is primed using custom hairpin primers that contain a universal PCR primer sequence (green), a restriction site (red) and a random 9-mer (blue).

Step 2: Primed material from Step 1 is PCR amplified using a universal primer.

Step 3: Amplified DNA from Step 2 is restricted with BciVI to generate 3'A overhang for ligation to Illumina adapters.

Figure 1A:
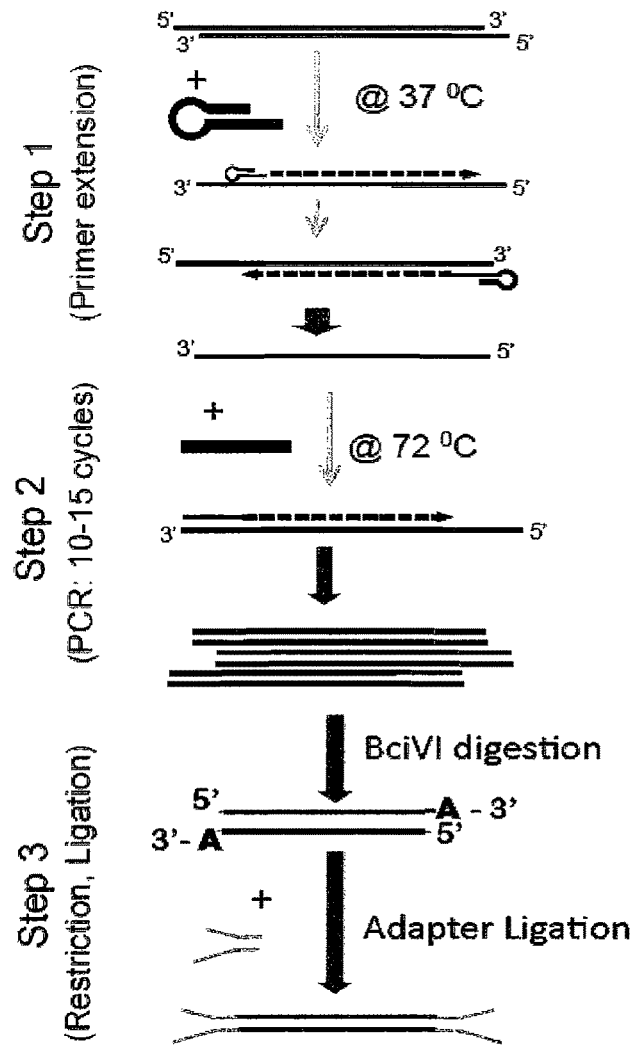
FIG. 1A: Schematic of Nano-ChIP-Seq library preparation.
Figure 1B:
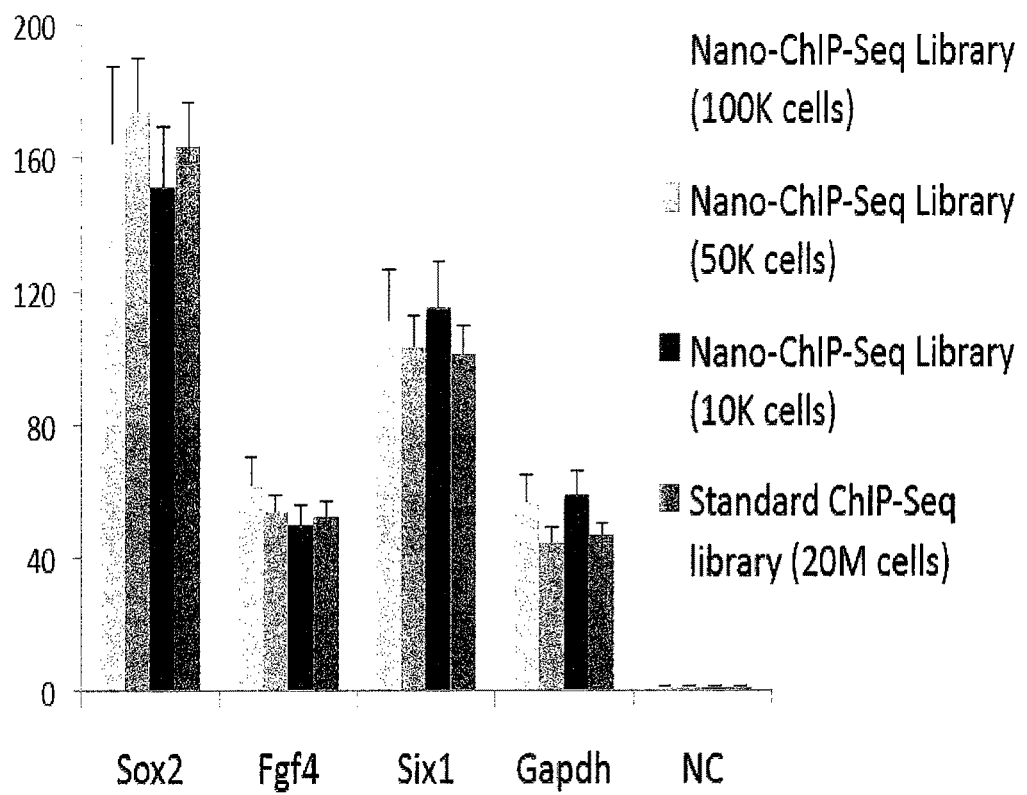
FIG. 1 illustrates one embodiment of a Nano-ChIP-Seq preparation of a sequencing library from scarce ChIP samples.

FIG. 1B: Quantitative PCR for validation and quality control of sequencing libraries. Bar graph shows enrichment of gene promoters known to carry K4me3 in ES cells, relative to a negative genomic control (y axis=fold enrichment). Data are shown for sequencing libraries derived from indicated small cell number ChIPs, compared to a standard ChIP-Seq library generated from a non-limiting sample size FIG. 2 presents exemplary data showing validation of Nano-ChIP-Seq chromatin maps.

Figure 2A:
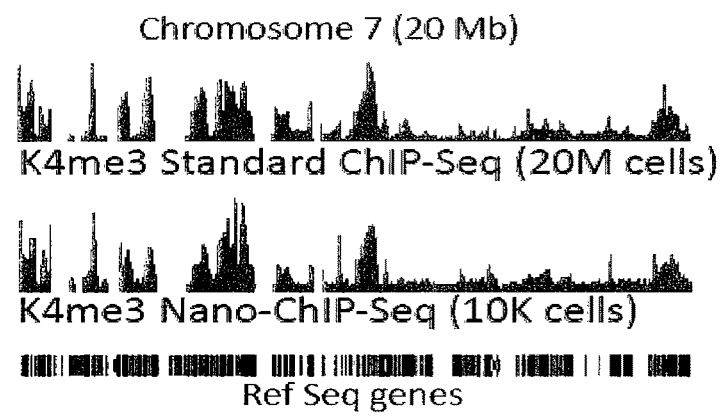

FIG. 2A: A comparison of K4me3 promoter signal tracks derived by ChIP-Seq (20 million cells) or Nano-ChIP-Seq (10 thousand cells) is shown for a 20 Mb region of chromosome 7. RefSeq genes are indicated below.

Figure 2B:
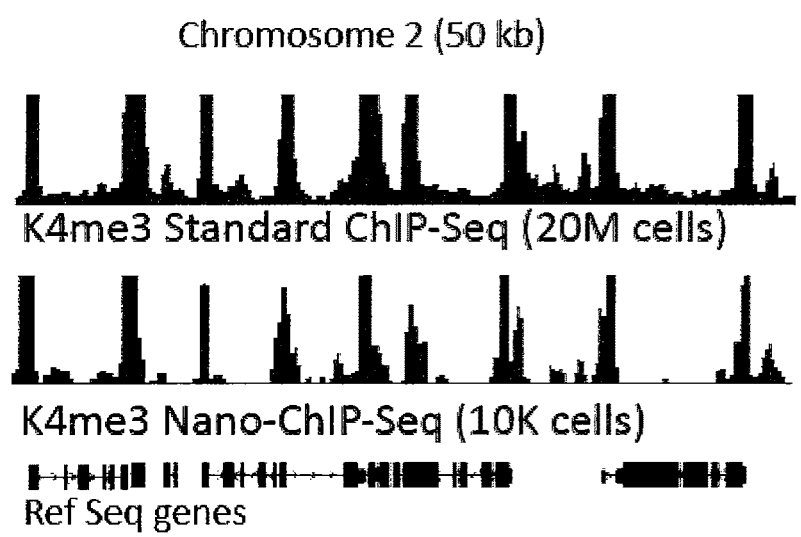

FIG. 2B: A comparison of K4me3 promoter signal tracks derived by ChIP-Seq (20 million cells) or Nano-ChIP-Seq (10 thousand cells) are shown for a 50 kb region of chromosome 2. Sites of K4me3 enrichment are evident at multiple gene promoters.

Figure 2C:
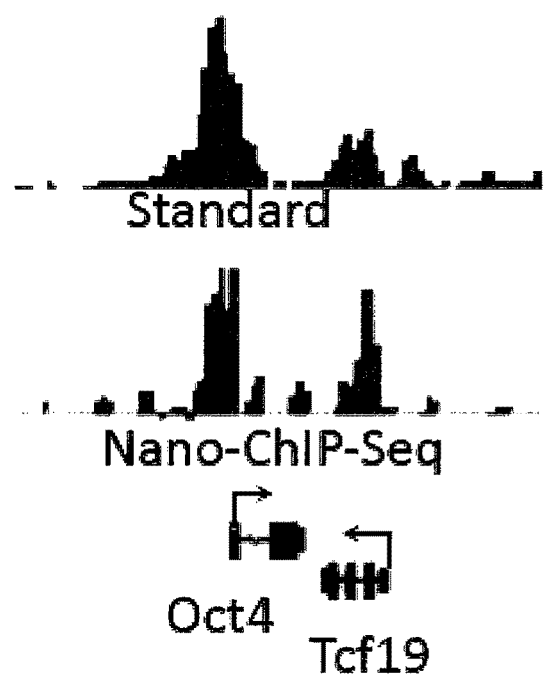

FIG. 2C: Comparison of K4me3 promoter signal tracks derived by ChIP-Seq (20 million cells) or Nano-ChIP-Seq (10 thousand cells) are shown for the locus encoding the pluripotency gene Oct4.

Figure 2D:
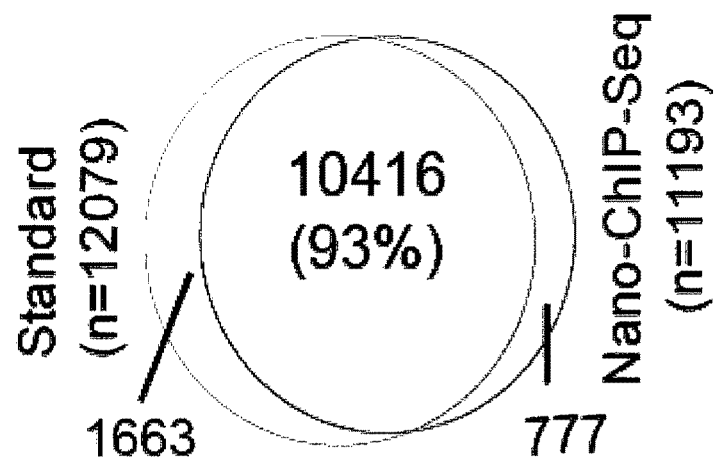

FIG. 2D: Venn diagram showing a 93% overlap between K4me3-marked promoters as determined by Standard ChIP (i.e., ChIP-Seq (20 million cells)) or Nano-ChIP-Seq (10 thousand cells).

Figure 2E:
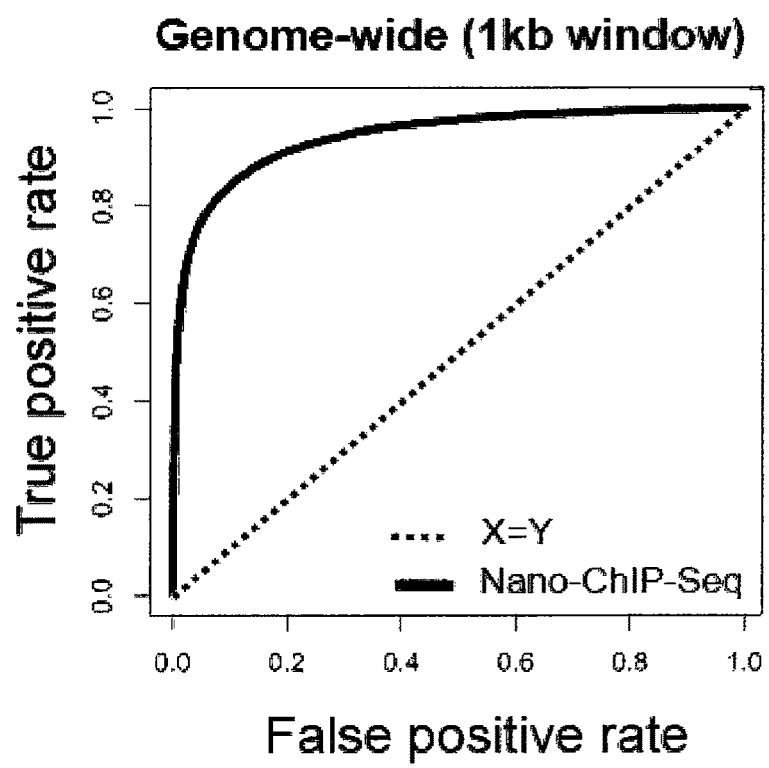

FIG. 2E: Receiver operating characteristic (ROC) curve for sensitivity and specificity analysis of K4me3 Nano-ChIP-Seq data. K4me3 enriched windows were collated using the non-limiting ChIP-Seq dataset as a gold standard. The ROC curve shows true positive and false positive rates for Nano-ChIP-Seq data at varying thresholds. This analysis suggests that Nano-ChIP-Seq has a sensitivity of at least 85% at a specificity of 90%.

FIG. 3 presents exemplary data wherein genome-wide Nano-ChIP-Seq chromatin maps for hematopoietic stem and progenitor cells (HSC) highlight developmental regulators.

Figure 3A:
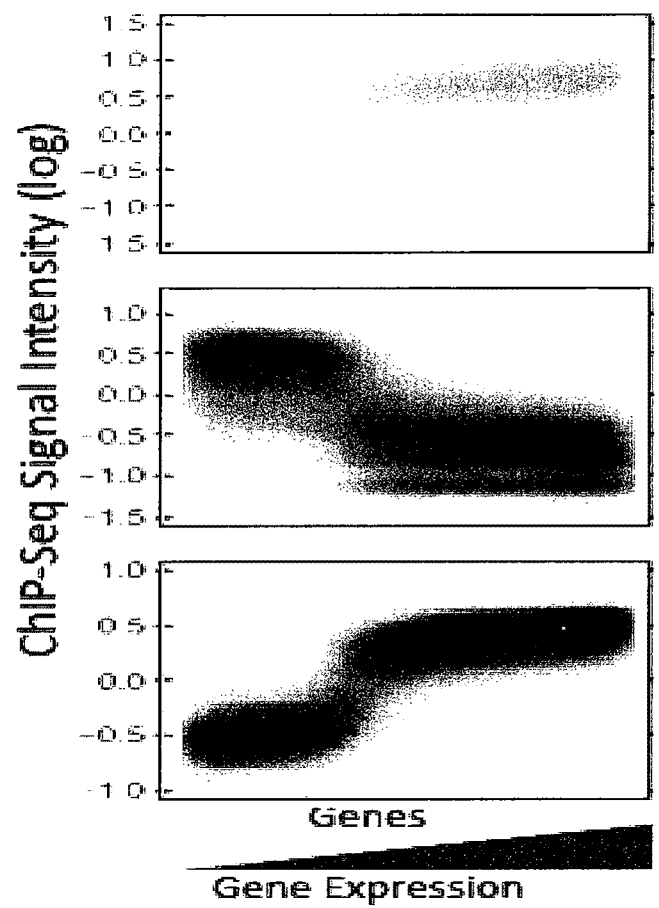

FIG. 3A: Scatterplots depict correlations between promoter K4me3 (green), promoter K27me3 (red), and gene body K36me3 (blue) methylation levels and mRNA expression in LSKs. Each datapoint corresponds to a single gene. Genes are rank ordered along the x-axis from high to low expression.

Figure 3B:
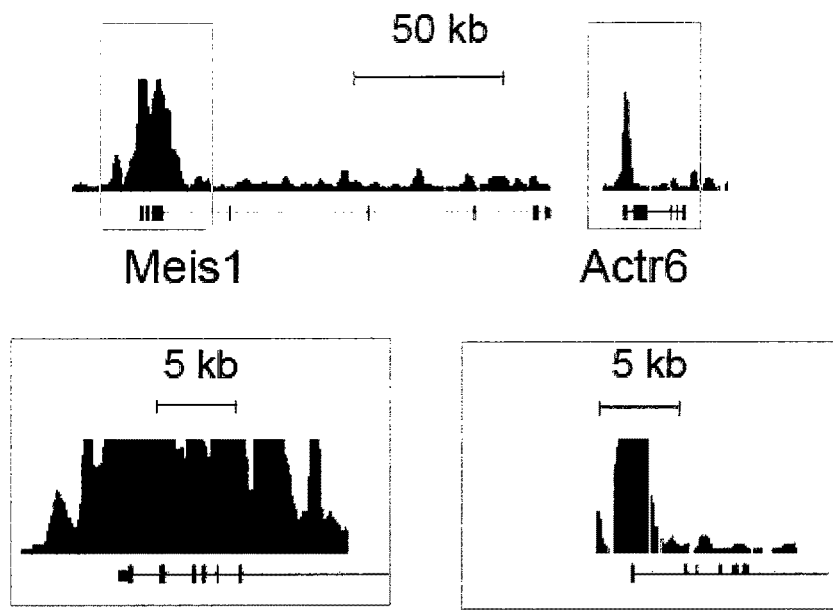

FIG. 3B: K4me3 signal tracks for HSCs show a broad K4me3 domain over the Meis1 promoter and a more typical punctuate peak over the Actr6 promoter.

Figure 3C:
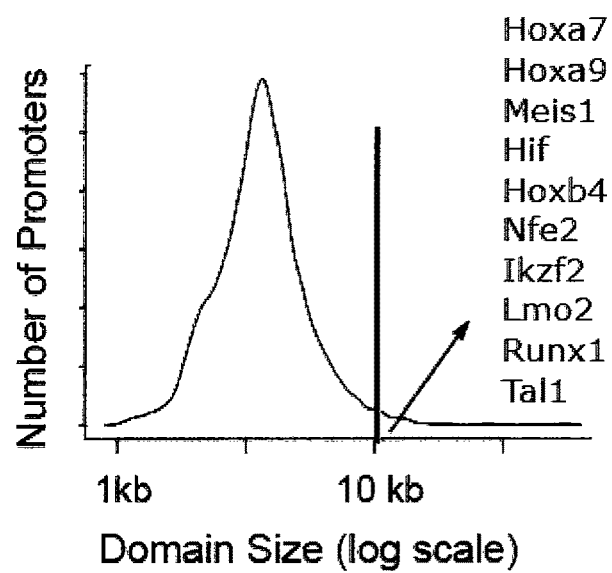

FIG. 3C: Histogram shows the size distribution of K4me3 enriched regions coincident with gene promoters in HSCs. Large K4me3 domains tend to coincide with promoters of some hematopoietic regulator genes.

Figure 3D:
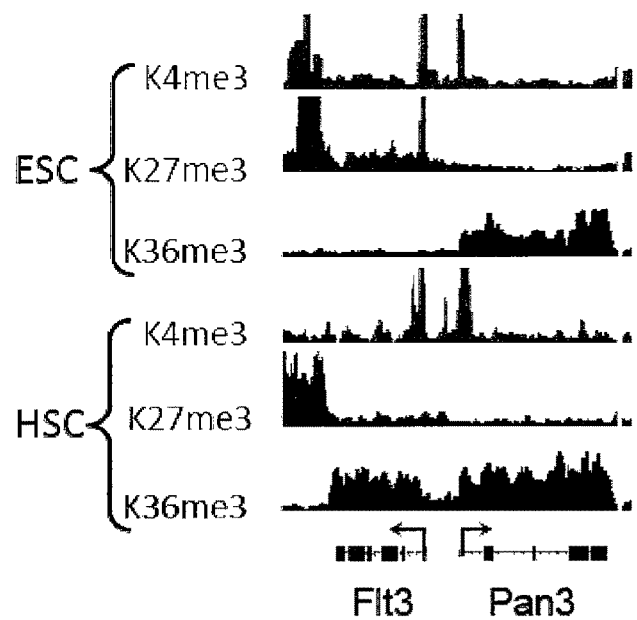

FIG. 3D: Tracks depict K4me3 (green), K27me3 (red) and K36me3 (blue) enrichment signals across developmental loci in ES cells and HSCs. Flt3 and genes in the HoxA cluster are bivalent in ES cells, but marked by large K4me3 domains in the hematopoietic progenitors (HSCs).

Figure 3E:
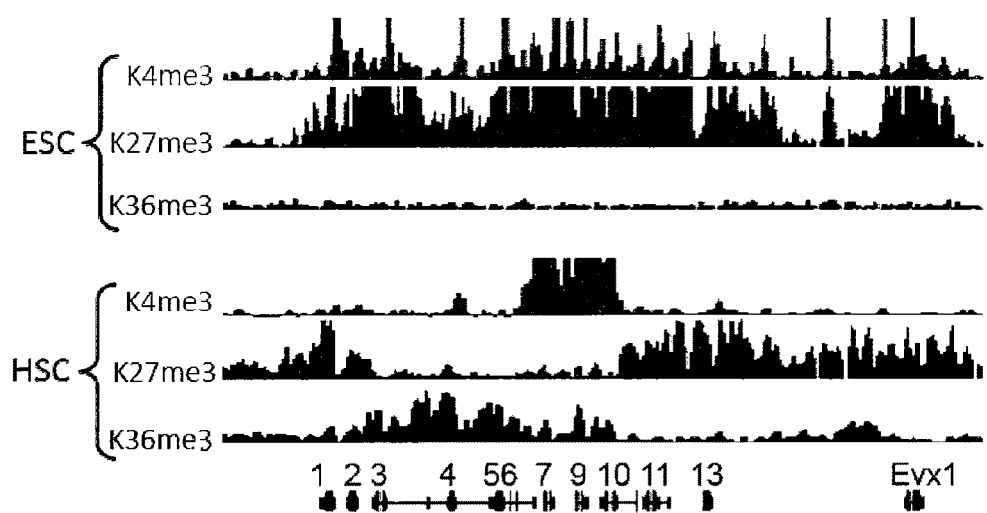

FIG. 3E: Tracks depict K4me3 (green), K27me3 (red) and K36me3 (blue) enrichment signals across developmental loci in ES cells and HSCs. Flt3 and genes in the HoxA cluster are bivalent in ES cells, but marked by large K4me3 domains in the hematopoietic progenitors (HSCs).

FIG. 4 presents exemplary data showing that gene potential may be predicted by chromatin state.

Figure 4A:
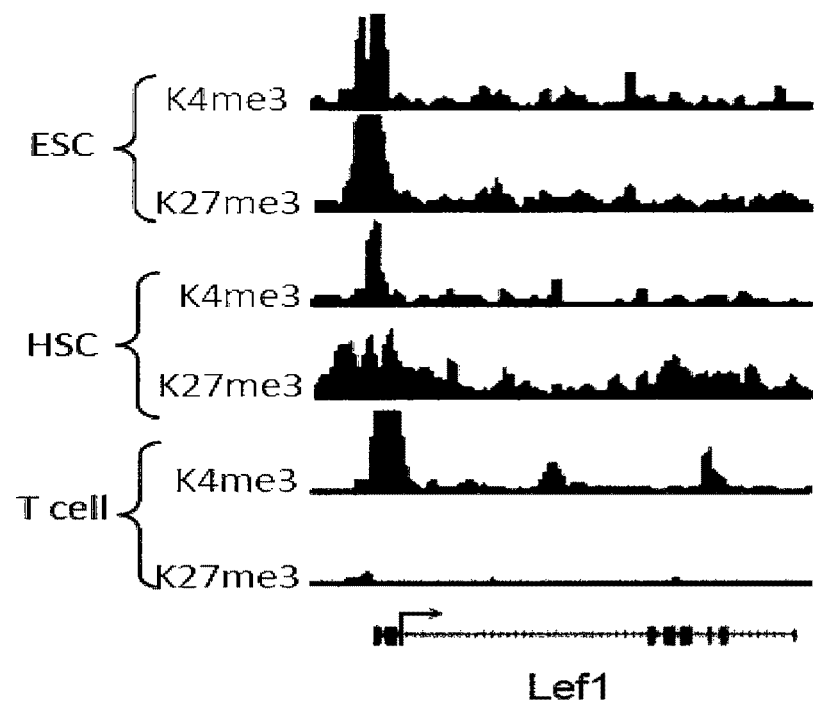

FIG. 4A: Tracks depict K4me3 (green), K27me3 (red) and K36me3 (blue) signals in ES cells, HSCs and CD4+ T-cells. Lef1, a T-cell regulator, is bivalent in ES cells and HSCs but carries active chromatin in T-cells.

Figure 4B:
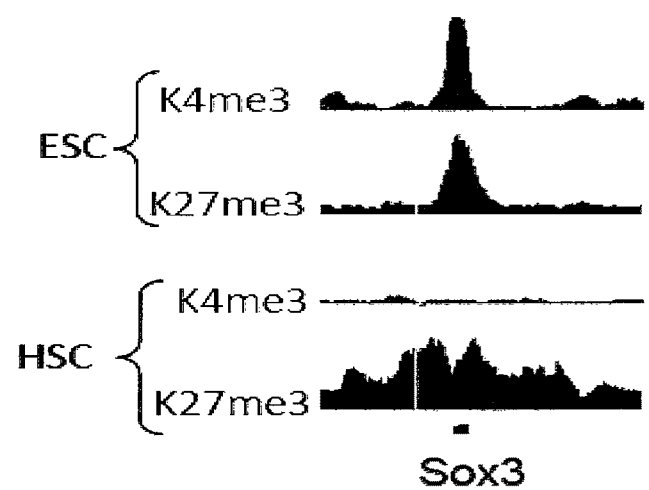

FIG. 4B: Sox3, an embryonic neural regulator, is also bivalent in ES cells, but is marked exclusively by K27me3 in HSCs and T-cells.

Figure 4C:
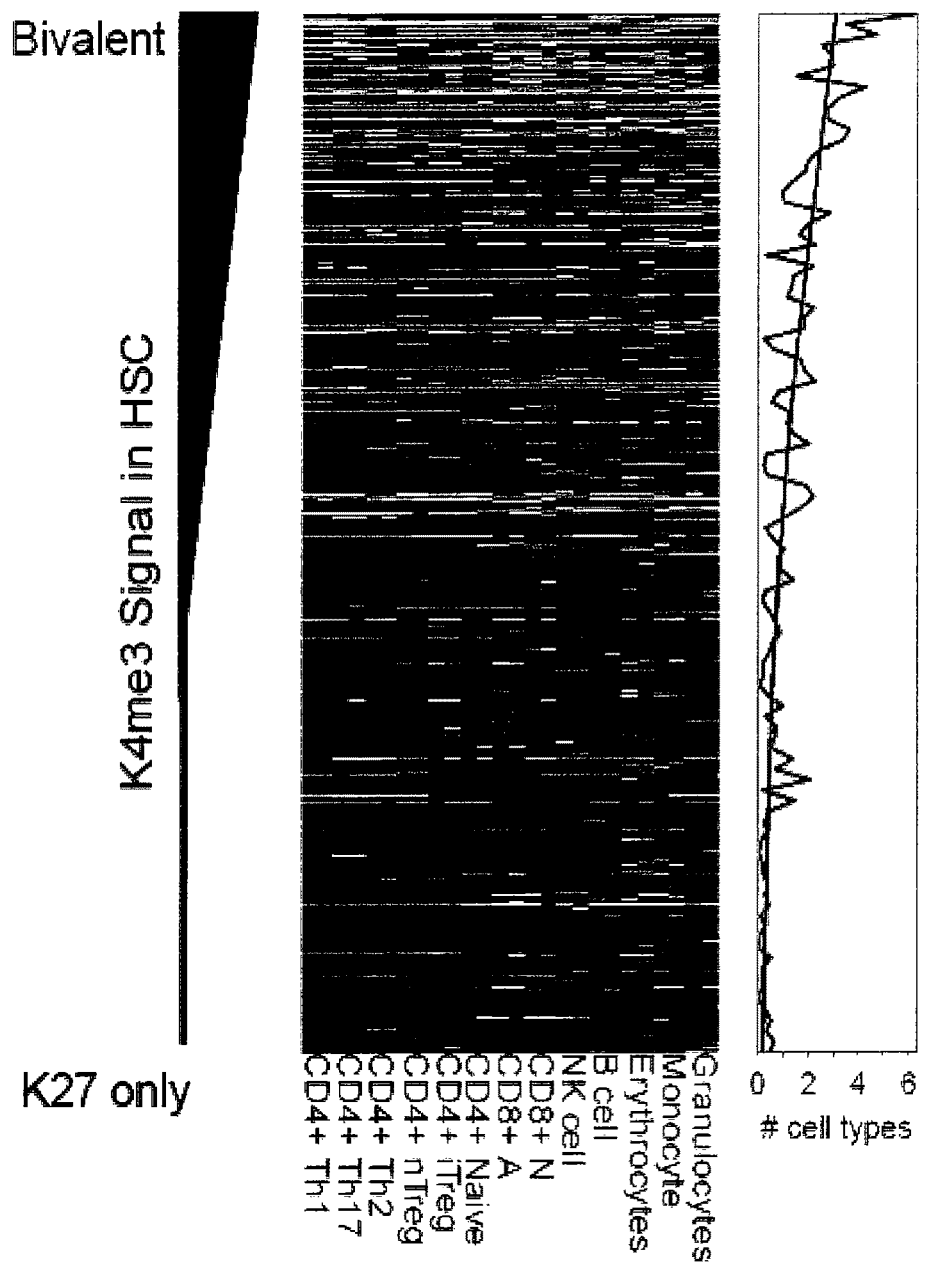

FIG. 4C: Heat map depicts the relationship between K4me3 signal in HSCs and gene expression in differentiated progeny. Promoters with K27me3 in HSCs are ranked according to K4me3 levels. Horizontal bars indicate transcript level of the corresponding gene in the indicated cell population (blue indicates low expression; red indicates high expression). The number of lineages in which a given gene is expressed is plotted vertically in the panel at right.

FIG. 5 presents two representative restriction enzymes capable of creating a single nucleic acid overhang, wherein cleavage occurs at the fifth nucleic acid from the end of the restriction binding site (SEQ ID NO. 15-GTATC-CNNNNNNN, SEQ ID NO. 16-CATAGGNNNNNNN).

FIG. 5A: BciVI

FIG. 5B: BfuI

Figure 6:
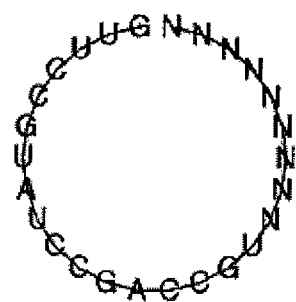
Figure 6:
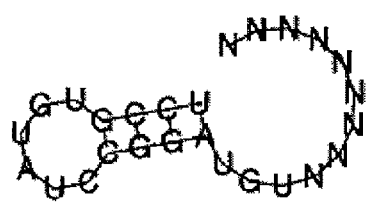
Figure 6:
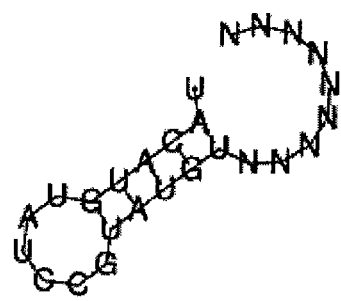
Figure 6:
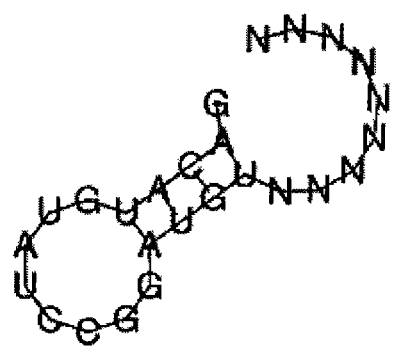

FIG. 6 presents several embodiments of primary and secondary structure for primer designs tested for optimization. Note: In some embodiments, the U's may be replaced with T's.

FIG. 6A: One embodiment of a conventional circular primer comprising twenty-six nucleic acid residues (SEQ ID NO. 17-GUUCCGUAUCCGAC CGUNNNNNNNNN).

FIG. 6B: One embodiment of a hairpin primer (HP1) comprising an eight nucleic acid residue closed loop, a fourteen nucleic acid residue open loop, wherein the closed loop and open loop are connected by a di-nucleotide duplex segment (SEQ ID NO. 18-UCCGUGUAUCCGGAU-GUNNNNNNNNN).

FIG. 6C: One embodiment of a hairpin primer (HP2) comprising an eight nucleic acid residue closed loop, an eleven nucleic acid residue open loop with a single nucleic acid residue overhang (i.e., for example, U), wherein the closed loop and open loop are connected by a tri-nucleotide duplex segment (SEQ ID NO. 19-UACAUGUAUCCGUAU-GUNNNNNNNNN).

FIG. 6D: One embodiment of a hairpin primer (HP3) comprising a ten nucleic acid residue closed loop, an eleven nucleic acid residue open loop with a single nucleic acid residue overhang (i.e., for example, G), wherein the closed loop and open loop are connected by a di-nucleotide duplex segment (SEQ ID NO. 20-GACAUGUAUCCGGAU-GUNNNNNNNNN).

DETAILED DESCRIPTION OF THE INVENTION

The present invention is related to the field of genomics. In particular, the invention is related to genome-wide mapping and high throughput sequencing from a biological sample having a low number of cells. In some cases, a chromatin map identifying gene locations may be determined when using between approximately 1,000-100,000 cells. For example, histone-DNA modifications have been mapped in hematopoietic stem cells using a biological sample containing approximately 20,000 cells.

Whole genome mapping of protein-DNA interactions can be performed by combining chromatin immunoprecipitation (ChIP) with high-throughput sequencing (ChIP-Seq). However, current methods require large amounts of starting materials which precludes their application to small biological samples and/or rare cell types. In one embodiment, the present invention contemplates a method combining a high-sensitivity ChIP assay with at least one embodiment of the present invention for generating sequencing libraries to map histone modifications in as few as 10,000 cells. In one embodiment, the method contemplates generating a genome-wide chromatin map for a purified population of cells (i.e., for example, hematopoietic stem and progenitor cells), thereby gaining unique insight into their developmental program.

Other methods of isolating genomic fragments besides ChIP are also compatible with some embodiments of the present invention as described below. For example, methods including, but not limited to, DNA isolation, RNA isolation followed by cDNA preparation with reverse transcriptase, protein-RNA interaction studies (i.e., for example, RNA pull down followed by cDNA preparation with reverse transcriptase, or DNA amplification from formalin-fixed, paraffin embedded (FFPE) samples. Further, there are many different methods to further fragment these DNA samples in preparation for the extension and amplification steps described below (i.e., for example, DNAase digestion, RNAase digestion, restriction enzyme digestion, acid-base digestion, or sonication). In particular, DNA isolated from FFPE samples can be amplified with hairpin primers wherein libraries are prepared as described herein. Although it is not necessary to understand the mechanism of an invention, it is believed that in FFPE samples, the DNA is significantly damaged (i.e., for example, multiple strand breaks etc) such that normal PCR amplification is not effective. Random hairpin primers as described herein can amplify damaged and/or fragmented DNA from FFPE samples because the present invention is not dependent on an intact DNA strand.

In one embodiment, the present invention contemplates a method for preparing a DNA library by providing picogram quantities of starting DNA. Although it is not necessary to understand the mechanism of an invention, it is believed that this represents an improvement of several orders of magnitude over existing methods and thus greatly expands the types of biological samples and disease tissues that can be studied. In one embodiment, the method comprises customized primers. In one embodiment, the primers comprise a random nucleic acid sequence. In one embodiment, the primers comprise a restriction site nucleic acid sequence. In one embodiment, the method comprises digesting an amplified DNA sequence with a restriction enzyme such that the resultant DNA amplicons may be seamlessly introduced into a standard sequencing devices (i.e., for example, Illumina, or ABI) and/or protocols.

I. Hematopoietic Stem Cell Production

Hematopoiesis is believed to be a well-characterized and dynamic developmental system where a pool of rare hematopoietic stem cells (HSC) self-renew and/or differentiate progressively to give rise to many progenitor cells and functional blood cells. Ogawa M., "Differentiation and proliferation of hematopoietic stem cells" Blood 81(11):2844-2853 (1993); and Orkin et al., "Hematopoiesis: an evolving paradigm for stem cell biology" Cell 132(4):631-644 (2008). Cell sorting and purification techniques may facilitate identification and analysis of gene expression profiles of rare cell populations enriched for hematopoietic stem cells. Forsberg et al. "Differential expression of novel potential regulators in hemato-poietic stem cells" PLoS Genet. 1(3): e28 (2005). However, there have been only limited genome-wide chromatin studies in the hematopoietic system.

Genome-wide studies in differentiated blood cells, cell lines or relatively less purified cell populations enriched for hematopoietic stem cells have been reported. Barski et al., "High-resolution profiling of histone methylations in the human genome." Cell 129(4):823-837 (2007); Orford et al., "Differential H3K4 methylation identifies developmentally poised hematopoietic genes" Dev Cell 14(5):798-809 (2008); and Cui et al., "Chromatin signatures in multipotent human hematopoietic stem cells indicate the fate of bivalent genes during differentiation" Cell Stem Cell 4(1):80-93 (2009).

Using current ChIP techniques, study of chromatin states and/or genome-wide histone modifications of highly pure progenitors and hematopoietic stem cells is difficult due to the rarity of cell number in biological samples. In one embodiment, the present invention contemplates a Nano-ChIP-Seq method to study genome-wide histone modifications using cell sample sizes that were previously incompatible with conventional ChIP technology. The data presented herein utilize mouse LSK cells comprising highly purified and enriched hematopoietic stem and/or early progenitor cells (HSC/HPC or HSCs). As shown herein, the Nano-ChIP-Seq method is capable of constructing chromatin maps to identify genome-wide locations of several histone modifications including, but not limited to, H3K4me3 (Histone H3 Lysine 4 trimethylation), H3K27me3 and H3K36me3 using only approximately 25,000 LSK cells (i.e., for example, HSCs).

II. Histone-DNA Interactions

Living cells contain constitutive protein-DNA interactions that perform cellular functions including, but not limited to, gene expression, DNA repair and replication, chromosome segregation, or genome stability. One method, chromatin immunoprecipitation (ChIP), has been reported to be capable of studying in vivo protein-DNA interactions. O'Neill et al. "Immunoprecipitation of chromatin" Methods Enzymol 274: 189-197 (1996). ChIP technology may provide an analysis of histone modification patterns and/or a genomic distribution of other DNA binding proteins such as transcription factors. Further, immunoprecipitated DNA can be analyzed for: i) individual binding sites by polymerase chain reaction (PCR); or ii) large-scale analysis of protein-DNA interactions by hybridization to DNA microarray chips (e.g., ChIP-chip). Alternatively, immunoprecipitated DNA may be sequenced in a high throughput manner (e.g., ChIP-Seq).

The data presented herein demonstrates that this method is capable of generating a genome-wide chromatin state map from a biological sample comprising approximately 10,000 cells. This represents an approximate 1,000-fold improvement over the required source material quantity from current state-of-the-art methods (i.e., for example, ChIP-Seq). In one embodiment, the method further comprises determining copy number from limiting DNA samples (i.e., for example, laser captured microdissection). In one embodiment, the method further comprises sequencing nucleic acids from paraffin-embedded clinical samples.

III. Chromatin Immunoprecipitation Sequencing (ChIP-Seq)

Chromatin immunoprecipitation sequencing (ChIP-Seq) has become a standard tool for mapping histone modifications and transcription factors across mammalian genomes. Park, P. J., "ChIP-seq: advantages and challenges of a maturing technology" Nat Rev Genet. 10:669-80 (2009). The technique couples a genome fractionation based on structural epitopes in chromatin with high-throughput sequencing to identify enriched genomic regions. Methodologically, ChIP-Seq involves: (i) fixation of protein-DNA interactions in living cells; (ii) chromatin fragmentation; (iii) immunoprecipitation with antibody to a modified histone or a DNA binding protein; and (iv) isolation and sequencing of immunoprecipitated DNA.

However, the technique is plagued by inefficiencies at both the ChIP steps and the sequencing steps that translate into a requirement for large amounts of starting materials, typically on the order of millions-tens of millions of cells. The ChIP assay yields small amounts of DNA whose availability for downstream assays is further reduced by DNA damage introduced during fixation and fragmentation. Although locus-specific analysis has been achieved for small cell numbers by coupling ChIP with PCR or arrays, such assays enrich target regions weakly and yield scarce quantities of DNA, and thus cannot be scaled to whole genome analysis. Dahl et al., "Q2ChIP, a quick and quantitative chromatin immunoprecipitation assay, unravels epigenetic dynamics of developmentally regulated genes in human carcinoma cells" *Stem Cells* 25:1037-1046 (2007); Acevedo et al., "Genome-scale ChIP-chip analysis using 10,000 human cells" *Biotechniques* 43:791-797 (2007); O'Neill et al., "Epigenetic characterization of the early embryo with a chromatin immunoprecipitation protocol applicable to small cell populations" *Nat Genet.* 38:835-841 (2006); and Attema et al., "Epigenetic characterization of hematopoietic stem cell differentiation using mini-ChIP and bisulfite sequencing analysis" *Proc Natl Acad Sci USA* 104:12371-12376 (2007).

A second major obstacle is that protocols for generating sequencing libraries require relatively large amounts of DNA, in part due to an inefficient ligation step that requires double-stranded DNA with intact ends. Overcoming these inherent limitations could greatly increase the applicability of the ChIP-Seq assay by enabling the analysis of rare cell populations (i.e., for example, primary hematopoietic stem cells).

Histone modifications have been implicated in the regulation of gene expression and genome function. Recent genome-wide technologies using ChIP-Seq have been utilized to study epigenetic information. Chromatin state maps generated by ChIP-Seq technology in embryonic stem (ES) cells and other cell lines have revealed information about gene regulation, genome biology and developmental potential of a given cell type. Barski et al. "High-resolution profiling of histone methylations in the human genome." *Cell* 129 (4):823-837 (2007); and Mikkelsen et al., "Genome-wide maps of chromatin state in pluripotent and lineage-committed cells." *Nature* 448(7153):553-560 (2007). However, ChIP-Seq has insufficient efficiency to provide chromatin state maps of small populations of biological cells including, but not limited to, small biopsies, FACS-sorted, or isolated primary stem and/or progenitor cells. While some epigenomic studies have tried using ChIP-Seq technology with 5-20 million cell samples, many biologically relevant cell populations are only available at amounts several magnitudes less (i.e., for example, 1,000-100,000 cells per sample). Sample sizes comprising cells between 1-100K are not sufficient to construct reliable chromatin maps using conventional ChIP-Seq methodologies.

For example, major problems of current ChIP-Seq technology include, but are not limited to: i) a high cell number requirement (i.e., for example, approximately $10^7$ cells/epitope); and ii) a large sample size to support most high-throughput sequencing library preparations (i.e., for example, approximately 5 ng). In some embodiments, the present invention contemplates methods that solve these problems. In one embodiment, the present invention contemplates a Nano-ChIP-Seq method comprising providing a biological sample comprising approximately 10,000 cells (i.e., for example, mouse embryonic stem cells). In one embodiment, the present invention contemplates a composition comprising a genomic DNA library based upon approximately 10,000 cells (i.e., for example, mouse embryonic stem cells). Mouse embryonic stem cell chromatin state maps constructed by the present invention were compared with conventional ChIP-Seq techniques using a much larger cell sample (i.e., for example, $10-20\times10^6$ cells) and were found to be highly concordant (data not shown).

Some research has developed modified quantitative ChIP protocols (i.e., for example, $Q^2$ChIP) that uses PCR to measure histone modifications on gene promoters using between $10^2$-$10^5$ cells. It should be noted that some experiments were performed using a sonicated chromatin equivalent of cells. Dahl et al., "$Q^2$ChIP, a quick and quantitative chromatin immunoprecipitation assay, unravels epigenetic dynamics of developmentally regulated genes in human carcinoma cells" *Stem Cells* 25(4):1037-1046 (2007). A carrier ChIP protocol (CChIP) has also been reported that used approximately $10^3$ cells in an analysis mixing a large number of *Drosophila* cells with small number of mammalian cells. O'Neill et al., "Epigenetic characterization of the early embryo with a chromatin immunoprecipitation protocol applicable to small cell populations" *Nat Genet.* 38(7):835-841 (2006).

While useful as a technical resource, ChIP-chip or ChIP-Seq technology is unsuitable when using carrier chromatin for large scale analysis. Carrier DNA is believed to constitute most of sequencing reads in ChIP-Seq and would potentially cross-react with DNA microarrays, thereby creating false positive signals in ChIP-chip experiments. One large scale ChIP-chip analysis of histone modification has been reported using $10^4$ cells. Acevedo et al., "Genome-scale ChIP-chip analysis using 10,000 human cells." *Biotechniques* 43(6): 791-797 (2007). Successive rounds of PCR amplification were required to obtain milligram amounts of source material from minute ChIP DNA samples. While PCR amplification of small amount of immunoprecipitated DNA might not introduce a bias in ChIP-chip analysis, this method is not ideal for ChIP-Seq technology as high throughput sequencing is more sensitive to PCR induced biases and also requires a special library preparation step.

In one embodiment, the present invention contemplates a Nano-ChIP-Seq method comprising providing a small number of cells, major modifications and miniaturation of a conventional ChIP method, and incorporating a small amount of immunoprecipitated DNA into a sequencing library. Although it is not necessary to understand the mechanism of an invention, it is believed that a small scale ChIP experiment from $10^4$ cells typically yield approximately 30 pg of immunoprecipitated DNA. Acevedo et al., "Genome-scale ChIP-chip analysis using 10,000 human cells." *Biotechniques* 43(6):791-797 (2007). Preliminary data demonstrate that source material comprising less than approximately 2 nanograms of immunoprecipitated DNA typically fail in Solexa sequencing libraries (data not shown).

In some embodiments, the present invention contemplates an improved ChIP method for the isolation of small DNA fragments. In one embodiment, the ChIP method comprises a reduced sonication step, wherein sonication is performed for a period of between approximately 0.5-20 seconds, preferably between approximately 1-10 seconds, and more preferably approximately 5 seconds. In one embodiment, the sonication step is optimized for a specific cell type. In one embodiment, the sonication is performed in serial exposures, wherein the duration of each successive exposure is less than the previous exposure. Although it is not necessary to understand the mechanism of an invention, it is believed that this modified sonication step is more advantageous for small samples than conventional ChIP sonication steps that are of longer durations and at higher frequencies. For example, if small samples are overexposed to sonication, the DNA fragments are too small and dissociate from the antibodies during the ChIP analysis. Further, higher centrifugation speeds are necessary due to the reduced sample size, as well as smaller assay vials (i.e., for example, a siliconized coated assay vial) wherein approximately 10,000 cells may be exposed to reduced amounts of ChIP antibody.

In some embodiments, the present invention contemplates an improved ChIP method for the isolation of small DNA fragments. In one embodiment, the method comprises a column wash step. Although it is not necessary to understand the mechanism of an invention, it is believed that a conventional tube wash/centrifugation step results in an unacceptable loss of sample (i.e., for example, conventional washing starts with approximately 1.5 ng of DNA and finishes with approximately 1.0 ng DNA, a 50% loss in sample). Consequently, binding small DNA fragments to beads within a column allows for high efficiency washing. In one embodiment, the method the washed DNA fragments are eluted with phenol-chloroform-isoamyl alcohol.

IV. Construction of a Nano-ChIP-Seq Library

In one embodiment, the present invention contemplates a method for making genome-wide chromatin maps from as few as ten thousand cells. In one embodiment, the method comprises combining a high-sensitivity ChIP assay with a novel molecular and enzymatic scheme for generating sequencing libraries from scarce DNA samples. In one embodiment, the method further comprises characterizing a chromatin landscape of a first purified cell population with a second purified cell population. In one embodiment, the first purified cell population comprises hematopoietic stem cells. In one embodiment, the second purified cell population comprises progenitor cells. Although it is not necessary to understand the mechanism of an invention, it is believed that the present method is highly advantageous over currently known methods in that a two to three orders of magnitude increase in sensitivity enables a detailed study of many biologically and clinically relevant cell models that have been previously inaccessible due to inadequate sample size.

In one embodiment, the present invention contemplates a method comprising at least three enzymatic steps. In a first step, a special enzyme is used to extend any given template DNA with a first oligonucleotide primer comprising a random 9-mer nucleotide overhang (i.e., for example, a hairpin universal primer) to generate a template. During a second step, a second oligonucleotide primer (i.e., for example, a standard universal primer) is used to amplify the template. The first and second primers are customized so that they both contain the same restriction enzyme binding site. Consequently, the amplified DNA template (i.e., for example, amplicon) comprises identical 5' and 3' ends, wherein the 5' and 3' end contain the same restriction enzyme site. In a third step, an enzymatic digestion of 5' and 3' ends is performed by a restriction enzyme compatible with the 5' and 3' restriction binding sites. The method may yield blunt or sticky 3' and 5' ends depending on the choice of restriction enzyme.

The method can be used to generate DNA libraries from minute amounts of DNA, wherein the library comprises a plurality of amplicons having identical as well as non-identical sequencing adapters at the 5' and/or 3' ends. These template libraries can be used in essentially any method of nucleic acid analysis that requires further amplification, ligation or sequencing of the templates.

In one embodiment, the present invention contemplates a Nano-ChIP-Seq method that is compatible with a starting sample size of approximately 10,000 cells. Although it is not necessary to understand the mechanism of an invention, it is believed that starting material comprising approximately 10,000 cells represents a two to three order of magnitude improvement over the existing methods. To facilitate integration of this method into most high-throughput sequencing platforms, the present invention was reduced to practice on a dominant short read sequencing platform (i.e., for example, an Illumina Genome Analyzer).

A. Development of PCR Modified ChIP Enrichment

Preliminary experiments attempted optimization of the ChIP assay to enable reproducible shearing and immunoprecipitation of small samples, and to reduce sample loss at all steps in the procedure. For example, by reducing sample volumes, combining lysis and sonication, and titrating quantities of antibody and bead, an enriched target loci for histone H3 lysine 4 trimethylation (K4me3) performed on 10,000 mouse embryonic stem (ES) cells was obtained using this modified ChIP method.

Although the optimized ChIP procedure appropriately enriched target loci, the DNA yields were below the detection limit of fluorometry (i.e., for example, <100 picograms). This improved ChIP method thus remained incompatible with standard ChIP-Seq protocols which require several nanograms of ChIP DNA to prepare sequencing library.

Consequently, the next attempted optimization step was to develop a library preparation procedure that would be compatible with picogram DNA amounts. For example, a K4me3 ChIP analysis performed on 10,000 cells was estimated to yield between 10 and 50 picograms of DNA. Similar to conventional ChIP-PCR methods, a strategy coupling a random primer-based amplification procedure was tested first. Such an approach would be compatible with known microarrays and standard Illumina library preparation. However, sequenced libraries prepared by amplification was ineffective. For example, high numbers of unalignable reads were obtained that likely reflect random primer artifacts, false positive peaks, and a conspicuous absence of signal over GC-rich regions. Accordingly, the resulting chromatin maps did not replicate datasets generated previously from non-limiting samples.

B. Nano-ChIP-Seq

In order to evaluate the failure of ChIP-PCR to effectively produce chromatin maps, a series of strategies was implemented that were intended to overcome the above problems.

For example, a quantitative PCR (qPCR) validation step was introduced to evaluate whether a given sequencing library preserved the sequence representation of the original ChIP DNA. qPCR validation allowed rapid testing and optimization of ChIP and library preparation conditions. For example, a series of modified random primers were tested that carried bulky chemical groups or were designed to form secondary structures intended to prevent self-annealing. Such bulky groups may include, but are not limited to, a hairpin sequence attached to a primer sequence, a steroid molecule (i.e., for example, cholesterol), or biotin. For example, three hairpin primer designs were compared to primers wherein sterically bulky substituent groups such as biotin or cholesterol were attached. For comparison purposes, a convention circular primer was used as a control. See, FIG. 6A. Among the hairpin primer designs, the HP1 primer is structurally stronger than and HP2 which is structurally relatively weak. Compare, FIGS. 6B and 6C. A third hairpin design provided a hybrid of HP1 and HP2, designated HP3. See, FIG. 6D.

These primers were compared for DNA amplification efficacy and activity in a water negative control. The negative control is believed to identify non-specific amplification resulting from primer self-annealing contamination (i.e., for example, primer dimers). See, Table 2.

TABLE 2

Total DNA Yield After 20 Cycles Of PCR

|  | Negative Control (H$_2$O) | DNA (x 0.1 ng) |
|---|---|---|
| Circular Primer | 6 | 12.8 |
| HP1 | 5.2 | 10 |
| HP2 | 15.3 | 20 |
| HP3 | 3.6 | 17 |
| Circular Primer + biotin | 1.7 | 2.7 |
| Circular Primer + cholesterol | 4.4 | 9.3 |

The data demonstrate that HP1 was not efficient in total DNA yield (i.e., 1 ng) and HP2 yielded too much of DNA amplification in negative control sample (i.e., 1.53 ng). Surprisingly, HP3 provided lower negative control contamination and higher total DNA yield than the conventional circular primer, as well as both HP1 and HP2. Although it is not necessary to understand the mechanism of an invention, it is believed that the larger closed loop of HP3 provides an increased flexibility to the primer thereby allowing more efficient annealing to a template strand. It should be noted that adding a sterically bulky organic group to a conventional circular primer did not provide a better DNA amplification yield than a conventional circular primer.

This test-bed identified random primer hairpin structures and complementary PCR primers that could effectively amplify ChIP DNA while minimizing non-specific product. Notably, in addition to facilitating protocol development, the qPCR validation provides a general quality control for sequencing libraries that is particularly valuable when starting from scarce ChIP samples that cannot themselves be evaluated. This step quantifies short amplicons corresponding to positive- and negative-control genomic sites whose chromatin states are relatively invariant across cell types. Faithful libraries support amplification of positive and negative sites, with the former detected at relatively higher levels. Equal representation of positive and negative sites is suggestive of a failed ChIP assay, while a failure to detect negative sites indicates amplification failure with production of non-specific product.

Alternatively, different PCR conditions and enzymes were tested for their capacity to maintain sequence representation. Various additives, cycling conditions and a specific polymerase enzyme were identified that allowed faithful amplification of the ChIP DNA and maintained representation of GC-rich sequences. In one embodiment, the present invention contemplates a method amplifying DNA using a Sequenase® polymerase (US Biological). In one embodiment, the present invention contemplates a method amplifying DNA using a BCA polymerase (Takara Inc). Although it is not necessary to understand the mechanism of an invention, it is believed that a BCA polymerase has an advantage of thermostability, thereby not requiring re-addition of polymerase after each PCR cycle. However, data suggests that the BCA polymerase may prime DNA poorly as significantly less amplification was observed when compared to Sequenase® polymerase (data not shown). In one embodiment, the present invention contemplates a method amplifying DNA using a Taq DNA polymerase. Although it is not necessary to understand the mechanism of an invention, it is believed that Taq DNA polymerase has a disadvantage of inefficiently amplifying high "GC" content DNA. In one embodiment, the present invention contemplates a method amplifying DNA using a Phusion® polymerase. In one embodiment, the method further comprises an additive such as dimethylsulfoxide (DMSO). Although it is not necessary to understand the mechanism of an invention, it is believed that a when DMSO is added to a Phusion polymerase amplification, GC rich DNA regions are efficiently amplified. Further, exonuclease degradation of excess random primers was found to further reduce non-specific amplification.

In one embodiment, the present invention contemplates an amplified DNA comprising restriction enzyme sites (i.e., for example, a BciVI site) introduced near the 5' and 3' ends of the ChIP fragments. These tandem restriction sites yield double-stranded products with 3' "A" overhangs that could be readily ligated to Illumina adapters for sequencing. A variety of restriction enzymes are capable of cleaving nucleotide sequences that may leave an "A" overhang. See, Table 1.

TABLE 1A

Restriction Enzymes Leaving A
3' Single Nucleic Acid Overhang

| Enzyme | Site Code | Cleavage Site(/) | |
|---|---|---|---|
| BmrI | ACTGGG | A C T G G G N N N N N/ | SEQ ID NO. 21 |
|  |  | T G A C C C N N N N N/N | SEQ ID NO. 22 |
| HpyAV | CCTTC | C C T T C N N N N N N/ | SEQ ID NO. 23 |
|  |  | G G A A G N N N N N N/N | SEQ ID NO. 24 |
| MnlI | CCTC | C C T C N N N N N N N/ | SEQ ID NO. 25 |
|  |  | G G A G N N N N N N N/N | SEQ ID NO. 26 |
| BnVI | GTATCC | G T A T C C N N N N N N/ | SEQ ID NO. 27 |
|  |  | C A T A G G N N N N N N/N | SEQ ID NO. 28 |
| HphI | GGTGA | G G T G A N N N N N N N/ | SEQ ID NO. 29 |
|  |  | C C A C T N N N N N N N/N | SEQ ID NO. 30 |

TABLE 1A-continued

Restriction Enzymes Leaving A
3' Single Nucleic Acid Overhang

| Enzyme | Site Code | Cleavage Site(/) | |
|---|---|---|---|
| BfiI | ACTGGG | A C T G G G N N N N N/ | SEQ ID NO. 31 |
| | | T G A C C C N N N N/N | SEQ ID NO. 32 |
| BmrI | ACTGGG | A C T G G G N N N N N/ | SEQ ID NO. 33 |
| | | T G A C C C N N N N/N | SEQ ID NO. 34 |
| Hin4II | CCTTC | C C T T C N N N N N/ | SEQ ID NO. 35 |
| | | G G A A G N N N N/N | SEQ ID NO. 36 |
| BfuI | GTATCC | G T A T C C N N N N N N/ | SEQ ID NO. 37 |
| | | C A T A G G N N N N N/N | SEQ ID NO. 38 |
| AlwI | GGATC | G G A T C N N N N/N | SEQ ID NO. 39 |
| | | C C T A G N N N N N/ | SEQ ID NO. 40 |
| BccI | CCATC | C C A T C N N N N/N | SEQ ID NO. 41 |
| | | G G T A G N N N N N/ | SEQ ID NO. 42 |
| PleI | GAGTC | G A G T C N N N N/N | SEQ ID NO. 43 |
| | | C T C A G N N N N N/ | SEQ ID NO. 44 |
| AclWI | GGATC | G G A T C N N N N/N | SEQ ID NO. 45 |
| | | C C T A G N N N N N/ | SEQ ID NO. 46 |
| BinI | GGATC | G G A T C N N N N/N | SEQ ID NO. 47 |
| | | C C T A G N N N N N/ | SEQ ID NO. 48 |
| BspPI | GGATC | G G A T C N N N N/N | SEQ ID NO. 49 |
| | | C C T A G N N N N N/ | SEQ ID NO. 50 |
| PpsI | GAGTC | G A G T C N N N N/N | SEQ ID NO. 51 |
| | | C T C A G N N N N N/ | SEQ ID NO. 52 |
| BcefI | ACGGC | A C G G C N N N N N N N N N N N N/N | SEQ ID NO. 53 |
| | | T G C C G N N N N N N N N N N N N N/ | SEQ ID NO. 54 |

A Illumina Genome Analyzer was used to deep-sequence a Nano-ChIP-Seq library of K4me3 promoter signals performed on 10,000 ES cells. Approximately 10 million 36 base reads were obtained. However, initial alignments indicated that the first 9 bases of the sequencing reads had higher mismatch rates, possibly due to imperfect hybridization of random primers. Accordingly, subsequent alignments were performed using bases 10 to 36 of each read. Seven of the 10 million sequenced reads could be aligned to the mouse reference genome. Aligned reads were processed into a genome wide K4me3 profile using a pipeline developed previously for ChIP-Seq data.

1. Bivalent State Chromatin Analysis: Association of Promoter K4me3 Signals With K27me3-Marked Promoters The present invention is exemplified by bivalent chromatin state data demonstrating that a wide range of promoter K4me3 signals may be seen at K27me3-marked promoters in LSK cells. Such a technique provides an opportunity to explore the significance of bivalent chromatin states in an in vivo setting. In one embodiment, the present invention contemplates testing whether a specific promoter (i.e., for example, K4me3) influences the likelihood that a corresponding gene promoter (i.e., for example, K27me3) will be induced in differentiated progeny. Although it is not necessary to understand the mechanism of an invention, it is believed that the presence of bivalent chromatin modifications increases the likelihood of subsequent transcriptional induction upon differentiation in vivo. Conversely, the presence of a specific promoter signals in the absence of a corresponding gene promoter signal predicts a more stable repression within the lineage (i.e., for example, no induction in differentiated progeny). Although it is not necessary to understand the mechanism of an invention, it is believed that bivalent chromatin may either causally maintain transcriptional potential or be a reflection of transcriptional priming in a progenitor population.

The data presented herein characterizes chromatin state maps of mouse LSK (Lin-, Sca-1+, Kit+) cells, which are highly enriched for hematopoietic stem cells (HSCs), using a Nano-ChIP-Seq method from a mouse LSK sample containing approximately 25,000 cells. For example, the results mapped the following histone trimethylation modifications: i) H3 Lysine 4 trimethylation (H3K4me3); ii) Histone H3 Lysine 27 trimethylation (H3K27me3); and Histone H3 Lysine 36 trimethylation (H3K36me3). These data suggest that some genes associated with HSC function display an active chromatin state (i.e., for example, by identification of these H3K4me3 and H3K36me3 modifications). Visual analysis of the 10,000 ES cell K4me3 Nano-ChIP-Seq map suggested good concordance to a standard ChIP-Seq K4me3 dataset generated from roughly 20 million ES cells. See, FIG. 2A and FIG. B. Both ChIP-Seq and Nano-ChIP-Seq methods show punctuate peaks of K4me3 signal at a majority of GC-rich promoters. Further, there was also cordance between ChIP-Seq and Nano-ChIP-Seq at the more expansive K4me3 enriched regions at loci encoding pluripotency genes such as Oct4. See, FIG. 2C.

Also evaluated was the global correspondence between these respective K4me3 datasets in a more quantitative fashion. For example, based on K4me3 signal density at the promoter region, a set of 11,193 K4me3-enriched promoters from the Nano-ChIP-Seq dataset was compared to an analogous set of 12,079 promoters identified from the ChIP-Seq K4me3 dataset. See, FIG. 2D. This analysis revealed a roughly 93% overlap between the two promoter sets. A genome-wide relationship was also evaluated between the ChIP-Seq and Nano-ChIP-Seq datasets by quantifying and comparing enrichment in all 1 KB windows across the genome. Considering the non-limiting ChIP-Seq dataset as a gold standard, the Nano-ChIP-Seq dataset was estimated to have a sensitivity of at least 85% at a specificity of ~90%. See, FIG. 2E. Hence, Nano-ChIP-Seq analysis of 10,000 ES cells generates accurate chromatin maps with high sensitivity and specificity.

Highly differentiated hematopoietic lineages, such as T cells and B cells, may comprise genes that have bivalent chromatin modifications (i.e., for example, a co-existence of H3K4me3 and H3K27me3). Although it is not necessary to understand the mechanism of an invention, it is believed that multiple histone modifications is consistent with a readiness for later activation during differentiation. In contrast, a non-hematopoietic cell lineage may be expected to comprise genes expressing a repressive monovalent chromatin modification (i.e., for example, a non-paired H3K27me3 signal).

Alternatively, the Nano-ChIP-Seq method may be used to characterize a purified population of hematopoietic cells enriched for hematopoietic stem cells. Although in vitro stem cell models, including mouse and human ES cells, have been extensively characterized through application of ChIP-Seq, studies of ex vivo stem cell populations have not been possible due to the rarity of the cells. A purified population of "Lineage-, Sca-1+ and c-kit+" (LSK) cells from murine bone marrow was prepared. Uchida et al., "Rapid and sustained hematopoietic recovery in lethally irradiated mice transplanted with purified Thy-1.1 lo Lin-Sca-1+ hematopoietic stem cells" *Blood* 83:3758-3779 (1994); and Morrison et al., "The long-term repopulating subset of hematopoietic stem cells is deterministic and isolatable by phenotype" *Immunity* 1:661-673 (1994). A ChIP analysis was performed for K4me3 and two other major histone modifications—H3 lysine 27 trimethylation (K27me3) and H3 lysine 36 trimethylation (K36me3)—using roughly twenty thousand cells per assay. Next, the Nano-ChIP-Seq method was used to generate libraries from each ChIP sample, which were then sequenced on the Illumina Genome Analyzer. The three experiments yielded between 13 and 19 million reads, of which roughly 75% could be uniquely aligned to the mouse reference genome. An adapted ChIP-Seq analytical pipeline was then used to generate the first genome wide maps of K4me3, K27me3 and K36me3 for this enriched hematopoietic stem cell population.

Several lines of evidence suggest that the Nano-ChIP-Seq chromatin maps accurately reflect the true patterns of histone modification in the LSK population. For example, K4me3 is seen to localize in gene promoter regions, consistent with its well-known association to sites of transcriptional initiation. See, FIG. 3A, and Bernstein et al., "Genomic maps and comparative analysis of histone modifications in human and mouse" *Cell* 120:169-181 (2005). Further, K36me3 is seen to localize in gene transcript regions, consistent with its association to transcriptional elongation. See, FIG. 3A, Barski et al., "High-resolution profiling of histone methylations in the human genome" *Cell* 129:823-837 (2007); and Mikkelsen et al., "Genome-wide maps of chromatin state in pluripotent and lineage-committed cells" *Nature* 448:553-560 (2007). Overall the data show that the integration of published gene expression profiles for LSK cells confirms expected global correlations between K4me3 and K36me3 signal intensities and the transcriptional status of the corresponding gene. In contrast, K27me3 localizes to genes with low mRNA expression levels in LSK cells See, FIG. 3A.

The Nano-ChIP-Seq LSK maps were analyzed for insight into chromatin and genome regulation in hematopoietic progenitors. Notably, a small set of gene promoters were observed to be associated with remarkably large regions (i.e., for example, >10 kb) comprising K4me3, wherein these K4me3 domains were distinct from the sharp peaks observed for a vast majority of gene promoters. See, FIG. 3B. A set of 100 promoters were collated that coincide with the largest K4me3 domains in LSK cells. The corresponding gene set shows striking enrichment for known hematopoietic regulators, including HoxB4, HoxA7, HoxA9, Runx1, Meis1, Ikzf2 and Flt3. See, FIGS. 3C-3E. Although it is not necessary to understand the mechanism of an invention, it is believed that because this data was compiled through unbiased analysis of K4me3 maps wherein 30 of the 100 tested genes encode transcription factors or other developmental regulators with previously described functions in Hematopoiesis, it is thus likely that at least some of the remaining 70 genes have, as yet unappreciated, functions in hematopoietic development.

In one embodiment, the present invention contemplates a method identifying similar expression patterns of at least two proteins (i.e., for example, K27me3 and/or K4me3). It has been reported that protein co-expression patterns may represent stable epigenetic repression by Polycomb proteins, Schwartz et al., "Polycomb silencing mechanisms and the management of genomic programmes" *Nat Rev Genet.* 8:9-22 (2007). Although it is not necessary to understand the mechanism of an invention, it is believed that the similar expression patterns of some proteins may help keep silent genes poised for activation at later development stages. Initially discovered in pluripotent ES cells, such 'bivalent domains' have since been described in multipotent cells, including hematopoietic progenitors. Weishaupt et al., "Epigenetic chromatin states uniquely define the developmental plasticity of murine hematopoietic stem cells" *Blood* (2009); Azuara et al., "Chromatin signatures of pluripotent cell lines" *Nat Cell Biol* 8:532-538 (2006); Bernstein et al., "A bivalent chromatin structure marks key developmental genes in embryonic stem cells" *Cell* 125: 315-326 (2006); and Mikkelsen et al., "Genome-wide maps of chromatin state in pluripotent and lineage-committed cells" *Nature* 448:553-560 (2007).

A Nano-ChIP-Seq analysis comparing K27me3 and K4me3 signals revealed roughly 1900 bivalent promoters in LSKs. To gain insight into the functional significance of the bivalent state, chromatin maps were compared for cell types representing a range of developmental potency: i) pluripotent ES cells; ii) multipotent hematopoietic progenitors (LSK); and iii) committed CD4+ T-cells. Mikkelsen et al., "Genome-wide maps of chromatin state in pluripotent and lineage-committed cells" *Nature* 448:553-560 (2007); and Ku et al., "Genome wide analysis of PRC1 and PRC2 occupancy identifies two classes of bivalent domains" *PLoS Genet.* 4:e1000242 (2008) Wei et al., "Global mapping of H3K4me3 and H3K27me3 reveals specificity and plasticity in lineage fate determination of differentiating CD4+ T cells" *Immunity* 30:155-167 (2009).

Several predominant patterns of chromatin changes were identified across this spectrum. For example, a class of genes was identified that carry bivalent marks in ES cells, but that are transcribed in hematopoietic progenitors and, accordingly, carry promoter K4me3 and gene body K36me3 in the LSKs. See, FIG. 3D. Although it is not necessary to understand the mechanism of an invention, it is believed that this class of genes includes many of the aforementioned hematopoietic regulators marked by K4me3 domains. Further, a class of promoters that are bivalent in ES cells and hematopoietic progenitors were identified but resolve to the transcribed state in the T-cells. See, FIG. 4A. Additionally, a third class of promoters were identified that are bivalent in ES cells, but resolve to a K27me3-only state in the hematopoietic progenitors. See, FIG. 4B.

The wide range of K4me3 signals seen at K27me3-marked promoters in LSKs provides an opportunity to explore the significance of the bivalent state in an in vivo setting. Consequently, the obtained chromatin data was integrated with a compendium of gene expression profiles for differentiated hematopoietic cells. Chambers et al., "Hematopoietic fingerprints: an expression database of stem cells and their progeny" *Cell Stem Cell* 1:578-591 (2007). Focusing on K27me3-marked promoters, the K4me3 signal in LSK cells was significantly correlated with the number of differentiated cell types in which the corresponding transcript was detected. See, FIG. 4C. This suggests that the presence of bivalent chromatin modifications in multipotent hematopoietic progenitors correlates with an increased likelihood of transcriptional induction during in vivo differentiation. Conversely, the presence of K27me3 signals without correlated promoter K4me3 signals predict a more stable repression within the lineage. Although it is not necessary to understand the mechanism of an invention, it is believed that bivalent chromatin may causally maintain transcriptional potential in a progenitor population and might be a consequence of transcriptional priming in these cells. Bottardi et al., "Lineage-specific transcription factors in multipotent hematopoietic progenitors: a little bit goes a long way" *Cell Cycle* 6:1035-1039 (2007).

In one embodiment, the present invention contemplates a method comprising constructing genome-wide chromatin maps from as few as 10,000 cells. In one embodiment, the method further comprises combining a high-sensitivity ChIP assay with a novel molecular and enzymatic scheme for generating sequencing libraries from scarce DNA samples. In one embodiment, the method further comprises characterizing the chromatin landscape of a purified population of cells (i.e., for example, hematopoietic stem and progenitor cells). Specific advantages of the present invention over currently available technologies include, but is not limited to, a two to three order of magnitude increase in sensitivity that enables a detailed study of many biological and clinical cell models that have been previously inaccessible due to inadequate sample size. The above data further demonstrate that both mouse LSK and human CD34+ cells comprise comparable genome wide chromatin modifications. Although it is not necessary to understand the mechanism of an invention, it is believed that this similarity may be due to high HSC enrichment in both cell populations.

IV. Disease Identification Using Chromatin Map Comparisons

The biological significance of interactions of nuclear proteins with DNA in the context of gene expression, cell differentiation, or disease has immensely been enhanced by the advent of chromatin immunoprecipitation (ChIP). ChIP comprises a technique whereby a protein of interest is selectively immunoprecipitated from a chromatin preparation to determine the DNA sequences associated with it. ChIP has been widely used to map the localization of post-translationally modified histones, histone variants, transcription factors, or chromatin-modifying enzymes on the genome or on a given locus. In spite of its power, ChIP has for a long time remained a cumbersome procedure requiring large number of cells. These limitations have sparked the development of modifications to shorten the procedure, simplify the sample handling, and make the ChIP amenable to small number of cells. In addition, the combination of ChIP with DNA microarray, paired-end ditag, and high-throughput sequencing technologies has in recent years enabled the profiling of histone modifications and transcription factor occupancy on a genome-wide scale. Collas P., "The state-of-the-art of chromatin immunoprecipitation" *Methods Mol. Biol.* 567:1-25 (2009).

Epigenetics refers to mitotically and/or meiotically heritable variations in gene expression that are not caused by changes in DNA sequence. Epigenetic mechanisms regulate all biological processes from conception to death, including genome reprogramming during early embryogenesis and gametogenesis, cell differentiation and maintenance of a committed lineage. Key epigenetic players are DNA methylation and histone post-translational modifications, which interplay with each other, with regulatory proteins and with non-coding RNAs, to remodel chromatin into domains such as euchromatin, constitutive or facultative heterochromatin and to achieve nuclear compartmentalization. Besides epigenetic mechanisms such as imprinting, chromosome X inactivation, or mitotic bookmarking which establish heritable states, other rapid and transient mechanisms, such as histone H3 phosphorylation, allow cells to respond and adapt to environmental stimuli. However, these epigenetic marks can also have long-term effects, for example in learning and memory formation or in cancer. Erroneous epigenetic marks may be responsible for many diseases including diseases evident at birth or infancy or diseases becoming symptomatic later in life. Moreover, although epigenetic marks can be created early in development, adaptations occurring through life can also lead to many diseases including but not limited to, cancer. Delcuve et al., "Epigenetic control" *J Cell Physiol.* 219 (2):243-250 (2009).

In one embodiment, the present invention contemplates a method comprising constructing at least one Nano-ChIP-Seq genome-wide chromatin state map using a small population of biological cells (i.e., for example, between approximately 1,000 to 100,000 cells). In one embodiment, the method generates a first chromatin map comprising a normal cell population. In one embodiment, the method generates a second chromatin map comprising a diseased cell population. In one embodiment, the first chromatin map is compared with the second chromatin map, wherein a differential histone modification pattern is identified. In one embodiment, the differential histone modification pattern diagnoses a specific disease.

A. Cancer Diseases

In one embodiment, the present invention contemplates a method to diagnose and/or identify cancer cells. The cancer cells may be derived from the oral cavity and pharynx, the digestive system, the respiratory system, bones and joints (e.g., bony metastases), soft tissue, the skin, breast, the genital system, the urinary system, the eye and orbit, the brain and nervous system (e.g., glioma), or the endocrine system (e.g., thyroid). Lymphoma cells (e.g., cells associated with Hodgkin's disease and Non-Hodgkin's lymphoma), multiple myeloma cells, or leukemia cells (e.g., acute lymphocytic leukemia, chronic lymphocytic leukemia, acute myeloid leukemia, chronic myeloid leukemia, and the like) also can be used in the context of the inventive method.

Other methods of mapping DNA-protein interactions within a genome have been reported by fixing living cells to cross-link DNA and proteins, lysing the cells, and isolating chromatin by immunoprecipitation. In these methods, DNA is purified and a SAGE protocol is performed on the purified DNA to produce GMAT-tag sequences, which are compared to a genomic sequence of the living cells to map DNA-protein interactions. These methods further identify an active chromatin domain and a method of identifying aberrant chromatin acetylation, wherein chromatin immunoprecipitation is performed using an antibody recognizing acetylated histone protein. Zhao, K., "Method of identifying active chromatin domains" U.S. Pat. No. 7,527,970 (herein incorporated by reference).

It has been reported that the Su(var) 3-9 protein family may combine two of the most evolutionarily conserved domains of chromatin regulators: the chromo (Aasland, R. and Stewart, A. F., Nucleic Acids Res 23:3168 74 (1995); Koonin, E. V., et al., Nucleic Acids Res 23:4229 33 (1995)) and the SET (Jenuwein, T., et al., Cell Mol Life Sci 54:80 93 (1998)) domain. Whereas the 60 amino acid chromo domain represents an ancient histone-like fold (Ball, L. J., et al., EMBO J 16:2473 2481 (1997)) that directs eu- or heterochromatic localizations (Platero, J. S., et al., Embo J 14:3977 86 (1995)), the molecular role of the 130 amino acid SET domain has remained enigmatic. The SET protein domain may define a genetic family of mammalian chromatin regulators. Moreover, the characterization of other members of the group of SET domain genes, apart from HRX/ALL-1, help to explain the mechanisms which are responsible for structural changes in chromatin possibly leading to malignant transformation.

Consequently it has been suggested that some proteins (i.e., for example, SUV39H proteins, and variants thereof, or EZH2 proteins, and variants thereof) may be used to analyze the interaction of SET domain proteins with chromatin or with other members of heterochromatin complexes. The genes which have a SET domain may be involved in the chromatin-dependent occurrence of deregulated proliferation. These genes or the cDNAs derived therefrom, or partial or mutated sequences thereof, can thus be used in the treatment and diagnosis of diseases which can be attributed to such proliferation. Specifically, oligonucleotides coding for the SET domain as such or parts thereof may be used as diagnostic markers in order to diagnose certain types of cancer in which the SET domain is mutated. Jenuwein et. al., "Chromatin regulator genes" U.S. Pat. No. 7,252,968 (herein incorporated by reference).

It has been reported that the protein pRb2/p130 represses expression of the ER-α gene. Blocking pRb2/p130 expression or altering ER-α gene methylation to alter pRb2/p130 complex binding allows transcriptional activity of the ER-α gene to be restored. Detecting and regulating the methylation state of the ER-α gene, optionally together with detecting and regulating pRb2/p130 multimolecular complexes bound to the ER-α gene promoter, allows estrogen-insensitive breast cancer cells to be identified, so that an accurate prognosis can be obtained and an appropriate course of treatment administered. Also, inhibiting pRb2/p130, or altering the methylation pattern of the ER-α gene by targeting DNMT 1 In the pRb2/p130-E2F4/5-HDAC 1-DNMT1-SUV39H1 complex, allows estrogen-insensitive breast cancer cells to be converted to estrogen-sensitive breast cancer cells. Estrogen-sensitive breast cancer cells which are generally more susceptible to current anti-cancer treatments. Giordano A., "Methods of diagnosing, prognosing and treating breast cancer" U.S. Pat. No. 7,635,561 (herein incorporated by reference).

B. Neurological Diseases

It has been difficult to identify behavioral disorder disease-causing alleles in schizophrenia (SZ) and bipolar disorder (BD) candidate genes. One reason may be that responsible functional variants may exist in unidentified regulatory domains. With the advent of microarray technology and high throughput sequencing, however, it is now feasible to screen genes for such regulatory domains relatively easily by using chromatin immunoprecipitation-based methodologies, such as ChIP-chip and ChIP-seq. In ChIP-chip, regulatory sequences can be captured from chromatin immunoprecipitates prepared with antibodies against covalently modified histones that mark certain regulatory domains; DNA extracted from such immunoprecipitates can then be used as microarray probes. As a first step toward demonstrating the feasibility of this approach in psychiatric genetics, ChIP-chip methods may be used to identify regulatory domains in several candidate genes: NRG1, DTNBP1, DISC1, DAO, DAOA, PDE4B, and COMT. Immunoprecipitates were generated with antibodies to histone H3 acetylated at lysine 9 (H3K9Ac) and histone H3 monomethylated at lysine 4 (H3K4me1), which mark promoters and some enhancers, using fetal brain chromatin as a substrate. Several novel putative regulatory elements, as well as the core and proximal promoters for each gene, were enriched in the immunoprecipitates. Genetic variants within these regions would be of interest to study as potential disease-associated alleles. Pedrosa et al., "Survey of schizophrenia and bipolar disorder candidate genes using chromatin immunoprecipitation and tiled microarrays (CUP-chip)" *J Neurogenet.* 23(3):341-52 (2009).

Despite recent advances in the treatment of Parkinson disease (PD), levodopa remains the most effective and widely used therapy. A major limitation to the use of levodopa is the development of abnormal involuntary movements, termed levodopa-induced dyskinesia (LDID), following chronic levodopa treatment. Since recent studies have suggested that modifications of chromatin structure may be responsible for many long-lasting changes in brain function, post-translational modifications of striatal histones have been examined in two models of LDID: an acute murine model and a chronic macaque monkey model, both exposed to 1-methyl-4-phenyl-1,2,3,6-tetrahydropyridine (MPTP). In the primate model, which closely resembles human LDID, chronic levodopa and the appearance of LDID was associated with marked deacetylation of histone H4, hyperacetylation and dephosphorylation of histone H3, and enhancement of the phosphorylation of extracellular signal-regulated kinase (ERK). In the murine model of acutely rather than chronically induced LDID, dopamine depletion and levodopa treatment also induced deacetylation of histone H4 and phosphorylation of ERK, but histone H3 exhibited decreased trimethylation and reduced rather than enhanced acetylation. These data demonstrate striking changes in striatal histones associated with the induction of LDID in both animal models. The pattern of changes observed, as well as the behavioral features, differed in the two models. However, both models exhibit marked deacetylation of histone H4, suggesting that inhibitors of H4 deacetylation may be useful in preventing or reversing LDID. Nicholas et al., "Striatal histone modifications in models of levodopa-induced dyskinesia" *J Neurochem.* 106(1):486-494 (2008).

Results of chromatin immunoprecipitation with the enhancer-associated protein p300 followed by massively parallel sequencing, and map several thousand in vivo binding sites of p300 in mouse embryonic forebrain, midbrain and limb tissue has been reported. 86 of the identified sequences were processed in a transgenic mouse assay, which in nearly all cases demonstrated reproducible enhancer activity in the tissues that were predicted by p300 binding. These results indicate that in vivo mapping of p300 binding is a highly accurate means for identifying enhancers and their associated activities, and suggest that such data sets will be useful to study the role of tissue-specific enhancers in human biology and disease on a genome-wide scale. Visel et al., "ChIP-seq accurately predicts tissue-specific activity of enhancers" *Nature* 457(7231):854-858 (2009).

C. Cardiovascular Disease

Arterial thrombosis is a common disease leading to severe ischemia beyond the obstructing thrombus. Additionally, endothelial dysfunction at the site of thrombosis can be rescued by L-arginine supplementation or arginase blockade in several animal models. Exposure of rat aortic endothelial cells (RAECs) to thrombin upregulates arginase I mRNA and protein levels. Thrombin strikingly increased arginase I promoter and enzyme activity in primary cultured RAECs. Using different deletion and point mutations of the promoter, it was demonstrated that the activating protein-1 (AP-1) consensus site located at −3157 bp in the arginase I promoter was a thrombin-responsive element. Chromatin immunoprecipitation assay (ChIP) confirmed that transactivation was initiated upon thrombin stimulation by c-Jun and ATF-2 binding to the AP-1 site. Zhu et al., "Thrombin Induces Endothelial Arginase through AP-1 Activation" *Am J Physiol Cell Physiol.* 2009 Dec. 23. [Epub ahead of print]

D. Autoimmune Diseases

Common SNPs in the chromosome 17q12-q21 region are believed to alter the risk for asthma, type 1 diabetes, primary biliary cirrhosis, and Crohn's disease. Previous reports have linked the disease-associated genetic variants with changes in expression of GSDMB and ORMDL3 transcripts in human lymphoblastoid cell lines (LCLs). The variants also alter regulation of other transcripts, and this domain-wide cis-regulatory effect suggests a mechanism involving long-range chromatin interactions. Disease-linked haplotypes may identify putative causal DNA variants via a combination of genetic and functional analyses. For example, high-throughput resequencing of the region and genotyping of potential candidate variants may be performed. Next, additional mapping of allelic expression differences in Yoruba HapMap LCLs construct a fine-map of the cis-regulatory differences to a handful of candidate functional variants. Common disease alleles may be linked to changes in CTCF binding and nucleosome occupancy leading to altered domain-wide cis-regulation. Finally, a strong association between asthma and cis-regulatory haplotypes was observed in three independent family-based cohorts (p=1.78×10$^{-8}$). Multiple parallel allele-specific tools may be useful for the investigation of noncoding disease variants and functional fine-mapping of human disease-associated haplotypes. Verlaan et al., "Allele-specific chromatin remodeling in the ZPBP2/GSDMB/ORMDL3 locus associated with the risk of asthma and autoimmune disease" *Am J Hum Genet.* 85(3):377-393 (2009).

A systematic search for regulatory elements has been performed in a 3.5 Mb region on human chromosome 20q13.12, a region associated with a number of medical conditions such as type II diabetes and obesity. Six histone modifications were profiled alongside RNA polymerase II (PolII) and CTCF in two cell lines, HeLa S3 and NTERA-2 clone D1 (NT2/D1), by chromatin immunoprecipitation using an in-house spotted DNA array, constructed with 1.8 kb overlapping plasmid clones. In both cells, more than 90% of transcription start sites (TSSs) of expressed genes showed enrichments with PolII, di-methylated lysine 4 of histone H3 (H3K4me2), tri-methylated lysine 4 of histone H3 (H3K4me3) or acetylated H3 (H3Ac), whereas mono-methylated lysine 4 of histone H3 (H3K4me1) signals did not correlate with expression. No TSSs were enriched with tri-methylated lysine 27 of histone H3 (H3K27me3) in HeLa S3, while eight TSSs (4 expressed) showed enrichments in NT2/D1. Akan et al., "A histone map of human chromosome 20q13.12" *PLoS One* 4(2):e4479 (2009)

Human systemic lupus erythematosus (SLE) is believed to be an autoimmune disease characterized by autoantibodies to nuclear components with subsequent immune complex formation and deposition in multiple organs. Further, a combination of genetic and environmental factors may be required for disease development, but how the environment interacts with the immune system in genetically predisposed hosts to cause lupus is unclear. Recent evidence suggests that environmental agents may alter T cell chromatin structure and gene expression through effects on DNA methylation, a repressive epigenetic mechanism promoting chromatin inactivation, to cause lupus in people with the appropriate genetic background. DNA methylation is regulated by ERK pathway signaling, and abnormalities in ERK pathway signaling may contribute to immune dysfunction in lupus through epigenetic effects on gene expression. Epigenetic abnormalities, and in particular DNA demethylation, may be involved in the pathogenesis of idiopathic and some forms of drug-induced lupus. For example, an impaired ERK pathway signaling may contribute to the development of human lupus through effects on T cell DNA methylation. Gorelik et al., "Aberrant T cell ERK pathway signaling and chromatin structure in lupus" *Autoimmun Rev.* 8(3):196-198 (2009).

The existence of phenotypic differences between monozygotic (MZ) twins is a prime case where the relationship between genetic determinants and environmental factors is illustrated. Although virtually identical from a genetic point of view, MZ twins show a variable degree of discordance with respect to different features including susceptibility to disease. Discordance has frequently been interpreted in terms of the impact of the environment with genetics. In this sense, accumulated evidence supports the notion that environmental factors can have a long-term effect on epigenetic profiles and influence the susceptibility to disease. In relation with autoimmune diseases, the identification of DNA methylation changes in individuals who develop the disease, and the influence of inhibitors of DNA methyltransferases and histone modification enzymes in the development of autoimmunity may be useful in the epigenetics field. Ballestar E., "Epigenetics Lessons from Twins: Prospects for Autoimmune Disease" *Clin Rev Allergy Immunol.* 2009 Aug. 4. [Epub ahead of print].

V. Isolation & Purification of Nucleic Acids and Proteins

A. Detection of Nucleic Acids mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

The method most commonly used as the basis for nucleic acid sequencing, or for identifying a target base, is the enzymatic chain-termination method of Sanger. Traditionally, such methods relied on gel electrophoresis to resolve, according to their size, wherein nucleic acid fragments are produced from a larger nucleic acid segment. However, in recent years various sequencing technologies have evolved which rely on a range of different detection strategies, such as mass spectrometry and array technologies.

One class of sequencing methods assuming importance in the art are those which rely upon the detection of PPi release as the detection strategy. It has been found that such methods lend themselves admirably to large scale genomic projects or clinical sequencing or screening, where relatively cost-effective units with high throughput are needed.

Methods of sequencing based on the concept of detecting inorganic pyrophosphate (PPi) which is released during a polymerase reaction have been described in the literature for example (WO 93/23564, WO 89/09283, WO98/13523 and WO 98/28440). As each nucleotide is added to a growing nucleic acid strand during a polymerase reaction, a pyrophosphate molecule is released. It has been found that pyrophosphate released under these conditions can readily be detected, for example enzymatically e.g. by the generation of light in the luciferase-luciferin reaction. Such methods enable a base to be identified in a target position and DNA to be sequenced simply and rapidly whilst avoiding the need for electrophoresis and the use of labels.

At its most basic, a PPi-based sequencing reaction involves simply carrying out a primer-directed polymerase extension reaction, and detecting whether or not that nucleotide has been incorporated by detecting whether or not PPi has been released. Conveniently, this detection of PPi-release may be achieved enzymatically, and most conveniently by means of a luciferase-based light detection reaction termed ELIDA (see further below).

It has been found that dATP added as a nucleotide for incorporation, interferes with the luciferase reaction used for PPi detection. Accordingly, a major improvement to the basic PPi-based sequencing method has been to use, in place of dATP, a dATP analogue (specifically dATPα) which is incapable of acting as a substrate for luciferase, but which is nonetheless capable of being incorporated into a nucleotide chain by a polymerase enzyme (WO98/13523).

Further improvements to the basic PPi-based sequencing technique include the use of a nucleotide degrading enzyme such as apyrase during the polymerase step, so that unincorporated nucleotides are degraded, as described in WO 98/28440, and the use of a single-stranded nucleic acid binding protein in the reaction mixture after annealing of the primers to the template, which has been found to have a beneficial effect in reducing the number of false signals, as described in WO 00/43540.

B. Detection of Protein

In other embodiments, gene expression may be detected by measuring the expression of a protein or polypeptide. Protein expression may be detected by any suitable method. In some embodiments, proteins are detected by immunohistochemistry. In other embodiments, proteins are detected by their binding to an antibody raised against the protein. The generation of antibodies is described below.

Antibody binding may be detected by many different techniques including, but not limited to, (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

C. Remote Detection Systems

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, wherein the information is provided to medical personal and/or subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

D. Detection Kits

In other embodiments, the present invention provides kits for the detection and characterization of proteins and/or nucleic acids. In some embodiments, the kits contain antibodies specific for a protein expressed from a gene of interest, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

VI. Kits

In one embodiment, the present invention contemplates kits for the practice of the methods of this invention. The kits preferably include one or more containers containing a compositions to practice various methods of this invention. The kit can optionally include a container comprising a DNA fragment, wherein said fragment comprises a random nucleic acid sequence, a 3' restriction site, and a 5' restriction site, wherein said 3' and 5' restriction sites are identical. The kit can optionally include a container comprising a restriction enzyme that cleaves at the 3' restriction site and the 5' restriction site. In one embodiment, the DNA fragment is a primer. In one embodiment, the primer is a hairpin primer. The kit can optionally include an antibody having a high affinity for a chromatin epitope. The kit can optionally include enzymes capable of performing PCR (i.e., for example, DNA polymerase, Taq polymerase, primers, and/or restriction enzymes). The kit can optionally include enzymes capable of performing reverse transcription PCR(RT PCR), such as reverse transcriptase.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in preparing DNA fragments from small populations of cells (i.e., for example, between approximately 10,000-50,000 cells). In one embodiment, the instructions describe a modified chromatin immunoprecipitation method capable of generating soluble chromatin fragments having a size ranging between approximately 200-700 basepairs. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VII. Antibodies

The present invention provides isolated antibodies (i.e., for example, polyclonal or monoclonal). In one embodiment, the present invention provides monoclonal antibodies that specifically bind to chromatin epitopes. These antibodies find use in the detection methods described above.

An antibody against an epitope of the present invention may be any monoclonal or polyclonal antibody, as long as it can recognize the epitope. Antibodies can be produced by using a epitope of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against an epitope of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% CO2 gas. The antibody titer of the supernatant of a hybridoma culture can be measured according to the same manner as described above with respect to the antibody titer of the anti-protein in the antiserum. Separation and purification of a monoclonal antibody can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is cross linked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten. In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times. The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a protein expressed resulting from a virus infection (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

EXPERIMENTAL

Example 1

Cell Acquisition

Mouse V6.5 embryonic stem (ES) cells were grown for two passages on 0.2% gelatin-coated plates containing DMEM media supplemented with 15% FCS, LIF, penicillin-streptomycin, Glutamax (Invitrogen), nonessential amino acids and 2-mercaptoethanol in 5% CO2 at 37° C. "Lineage-, Sca-1+, c-kit+" (LSK) cells were enriched from murine bone marrow using a fluorescence-activated cell sorting (FACS) method on a Vantage Cell Sorter (Becton Dickinson, Mountain View, Calif.). Varnum-Finney et al., "Notch target Hes5 ensures appropriate Notch induced T-versus B-cell choices in the thymus" *Blood* 111:2615-2620 (2008).

Example II

High-Sensitivity ChIP Assay

Approximately 10,000 embryonic stem (ES) cells, counted with a haemocytometer, or approximately 20,000 FACS-sorted LSK cells were used for each ChIP assay.

Cells were cross linked with 1% formaldehyde in 1 ml phosphate buffered saline (PBS) at room temperature for 10 minutes. After quenching with glycine for 5 min, the cells were washed twice with ice cold PBS with 10% serum. The addition of serum enhanced cell recovery during the washing steps. Cells were collected after each wash by centrifugation at 5000 rpm for 3 min. Cell pellets were re-suspended in 100 µl of lysis buffer containing 1% SDS, 10 mM EDTA, 50 mM Tris-HCl (pH 8.1) and flash frozen and stored at −80° C.

At the time of the experiment, cells were thawed and kept on ice for 10 min to allow lysis. Lysate was then diluted with 400 µl of ChIP dilution buffer containing 0.01% SDS, 1.1% Triton X-100, 1.2 mM EDTA, 16.7 mM Tris-HCl (pH ~8.1). Lysis buffer was diluted before sonication for mini ChIP assays to ensure sufficient volume during sonication and prevent excessive lysis during sonication. Cells were then sonicated under conditions optimized to yield soluble chromatin fragments in a size range of 200 to 700 basepairs. Chromatin from 10,000 ES cells was sonicated for approximately 105 seconds using a Branson sonifier (Branson 250) at 40% power amplitude (pulses: 0.7 second "on", and 1.3 second "off"). Chromatin from 20,000 LSK cells was sonicated for approximately 150 seconds under the same conditions. After saving 10 µl (2%) of the lysate for input control, the samples were immunoprecipitated. Although standard ChIP protocols precipitate insoluble chromatin by centrifugation, this step results in substantial loss of materials when using small numbers of cells.

Solubilized chromatin was immunoprecipitated overnight in 1 ml ChIP Dilution buffer supplemented with protease inhibitor cocktails (Roche). Antibody quantities were reduced as compared to conventional assays for the 20,000 cell ChIP assays, as follows: 0.1 µg K4me3 (Millipore 07473); 0.2 mg K27me3 (Millipore 07449); 0.1 µg K36me3 (Abcam 9050). Excess antibody significantly increases background in the small quantity ChIP assay, presumably due to non-specific pulldown. After immunoprecipitation overnight, samples were incubated with ~10 µl of prewashed Protein A-Sepharose beads at 4° C. for 2 hours. After binding, the beads were collected by brief centrifugation at 1,000×g, keeping the unbound fraction to confirm fragmentation by gel electrophoresis.

The bound beads were successively washed twice with 700 µl of each of the following ChIP washing buffers at 4° C.: Low Salt Immune Complex Wash Buffer (0.1% SDS, 1% Triton X-100, 2 mM EDTA, 20 mM Tris-HCl, pH 8.1, 150 mM NaCl); LiCl wash buffer (0.25M LiCl, 1% NP40, 1% deoxycholate, 1 mM EDTA, 10 mM Tris-HCl, pH 8.1); and TE pH 8 (10 mM Tris-HCl, 1 mM EDTA, pH 8.0). In each case, beads were collected on filter columns (Costar 8160) to maximize recovery. The chromatin was eluted from the beads twice with 125 µl of ChIP elution buffer (0.2% SDS and 0.1 M NaHCO$_3$) supplemented with fresh DTT (5 mM final concentration) by incubating at 65° C. for 10 min and centrifugation at maximum speed for 1 min. The eluted chromatin as well as the "input" sample (supplemented with 240 µl Chip Dilution buffer, 10 µl of 5M NaCl, 25 µl 10% SDS and 1.25 µl 1M DTT) were then incubated at 65° C. for 5 hours and then digested with Proteinase K at 37° C. for 2 hours. The immunoprecipitated DNA was extracted once using phenol-chloroform-isoamyl alcohol and precipitated with ethanol and glycogen. Precipitated DNA was washed once with 70% Ethanol and incubated with RNAse A at 37° C. for 30 minutes.

Example III

Nano-ChIP-Seq Library Preparation

The library method described here is composed of three major steps:

Step 1: ChIP DNA from 10,000-2,000 cells (estimated at 10-50 picograms), prepared in accordance with Example II, is primed with a modified universal primer (i.e., for example, 5'-GACATGTATCCGGATGT↓NNNNNNNNN-3' (SEQ ID NO:1)) for four priming cycles to create template DNA with common primer sequence incorporated at both the 5' and 3' ends. The modified universal primer contains a common PCR sequence (italicized), a restriction site for BciVI (underlined sequence; arrow indicates location of BciVI restriction enzyme cleavage) and a random 9-mer at the 3' end (N . . . N). The priming is achieved using Sequenase V2.0 (US Biochemical 70775), and a DNA polymerase with strand displacement capability but no 3'→5' exonuclease activity. 7 µl of ChIP DNA was incubated with 1 µl of the modified universal primer (2 mM stock) and 2 ml of Sequenase buffer at 98° C. briefly, and then annealed at 8° C. for 10 min. Next, 5.5 µl of Sequenase Enzyme mix containing 1.5 µl of 3 nM dNTPs, 0.75 µl 0.1 M DTT, 500 mg/ml BSA and 0.3 µl 13 U/µl Sequenase was added to the ChIP DNA. The temperature was gradually increased to 37° C. and incubated for 8 min. The whole cycle was then repeated with the addition of 1.2 µl of diluted Sequenase (1:3) instead of the enzyme mix. After four cycles of priming, excess modified universal primer was cleaned up by exonuclease and alkaline phosphatase treatment.

Step 2: Product from the priming reaction of Step 1 was PCR amplified using a second primer (i.e., for example, 5'-GACATGTATCCGGATGT-3' (SEQ ID NO:2)). This second primer lacks the random 9-mer sequence as in the modified universal primer but contains the same restriction site codons (underlined portion). The PCR reaction contained 50 µl of priming reaction, 1 µl of the second primer (5 mM stock), 1.5 µl of Phusion DNA Polymerase (NEB), 15 µl of high GC buffer (NEB) and 1% DMSO. The amplification consisted of 15 cycles of denaturation (98° C. for 30 sec), annealing (40° C. for 30 sec and 50° C. for 30 sec) and extension (72° C. for 1 min).

Step 3: After overnight restriction with a restriction enzyme specific for the primer restriction sites (i.e., for example, BciVI (NEB)), yields 3' "polyA" overhangs at each end. Subsequently, the amplified product was ligated to Illumina adapters using the Quick Ligation Kit (NEB). This approach eliminates several prior steps in the standard Illumina library preparation, significantly reducing loss of materials.

The ligated fragments were amplified for 18 cycles using standard Illumina primers and were then size selected on a 1% agarose gel, retaining fragments between 275 and 600 bp. The resulting libraries were hybridized to flowcells, subjected to cluster amplification and sequenced by synthesis on the Illumina Genome Analyzer using standard procedures.

Example IV

Quality Control and Library Validation by qPCR

A qPCR-based quality control strategy was developed to assess whether sequencing Libraries maintained faithful representation of starting sample with minimal production of non-specific product.

A series of primers were designed that yield short amplicons (~80-100 bp). These primers were designed against genomic sites representing negative control regions that have not been seen to be modified in any cell type studied to date, as well as several positive control regions of varying G+C sequence contents that are frequently enriched for K4me3, K27me3 or K36me3.

The Library was also prepared from un-enriched chromatin to enable assessment of relative enrichment levels in qPCR by the ΔΔCT method. Primer sequences included, but are not limited to:

```
Six1-5':
TGATTGTGAGGCGAGAACTG        (SEQ ID NO: 3)

Six1-3':
GATCACCTGCACAAGAACGA        (SEQ ID NO: 4)

Gapdh-5':
CAAAGGCGGAGTTACCAGAG        (SEQ ID NO: 5)

Gapdh-3':
CTGCAGTACTGTGGGGAGGT        (SEQ ID NO: 6)

Sox2-5':
CAGGGAGTTCGCAAAAGTCT        (SEQ ID NO: 7)

Sox2-3':
TGGACATTTGATTGCCATGT        (SEQ ID NO: 8)

Fgf4-5':
TGGGTGTGATGCTGTTTCAT        (SEQ ID NO: 9)

Fgf4-3':
CTCAGGGTCCTTCTCACTGC        (SEQ ID NO: 10)

Negative Control-5':
AACCTCACACACAACAAGCTG       (SEQ ID NO: 11)

Negative Control-3':
TGTGATAGGGAGAATGCTTGC       (SEQ ID NO: 12)
```

Example V

Processing and Alignment of Nano-ChIP-Seq Sequencing Reads

Reads from high-throughput sequencing prepared in accordance with Example III were post-processed and aligned to the reference genome (UCSC, mm8) from the 10$^{th}$ base using MAQ (Mapping and Assembly with Quality) package with default parameters.

Reads that mapped to highly repetitive regions were filtered out. Multiple reads mapped at the same position were only counted once to remove potential bias from PCR. A density map was then established at a 25 bp resolution by counting the number of reads oriented towards each position and within a range of the average length of ChIP fragment (~300 bp, reads within 200 bp are counted by 1 and reads within 300 bp 0.25). Positions in the density map where less than 50% of the flanking 200 bp are alignable were masked as repetitive and disregarded from further analysis. A set of 19,149 RefSeq genes was then collated (See, NCBI, Mar. 13, 2008 update).

For each gene, promoter signals were calculated for K4me3 and K27me3 using the mean signal density over a 4 kb interval centered on the transcription start site. K36me3 signals were also calculated using the mean signal density over the gene body.

Example VI

Comparison of Conventional ChIP-Seq Data and Nano-Chip-Seq Data

A set of 11,193 K4me3-enriched promoters in the Nano-ChIP-Seq dataset and 12,079 enriched promoters in a standard ChIP-Seq dataset were collated based on density distributions.

A genome wide correspondence was also evaluated between the respective datasets by calculating the mean H3K4me3 ChIP-Seq densities for non-overlapping 1 kb windows across the genome. The top 20,000 1 kb windows in a standard K4me3 ChIP-Seq dataset were defined as 'positives' (e.g., this coverage approximates estimated K4me3 genome coverage). Considering these positives as a 'gold standard', true positive rates and false positive rates were calculated for the K4me3 Nano-ChIP-Seq dataset at varying cutoff values for Receiver Operating Curve (ROC) analysis.

Example VII

Analysis of Chromatin State Maps

Global correlations between chromatin state maps of LSK cells and gene expression levels were determined based on published gene expression profiles. Chambers et al., "Hematopoietic fingerprints: an expression database of stem cells and their progeny" *Cell Stem Cell* 1:578-591 (2007); Tothova et al., "FoxOs are critical mediators of hematopoietic stem cell resistance to physiologic oxidative stress" *Cell* 128: 325-339 (2007); and Wei et al., "Global mapping of H3K4me3 and H3K27me3 reveals specificity and plasticity in lineage fate determination of differentiating CD4+T cells" *Immunity* 30:55-167 (2009).

The original CEL files were processed with GCRMA (GC Robust Multiarray Average) package and quantile-normalized. H3K4me3 enriched intervals were called by a window-scan procedure. A background signal model was established by randomly moving each read to an alignable position on the same chromosome. Then, for each 1 kb window sliding across the genome, a nominal P-value was calculated by comparison with the random background. Windows with nominal P-value <10$^{-5}$ were identified as enriched and enriched windows separated by gaps of size <1 kb were merged.

We claim:

1. A method comprising:
    a) providing;
        i) a biological sample comprising less than 50,000 cells, wherein said biological sample comprises genomic DNA;
        ii) a hairpin primer comprising at least one restriction enzyme binding site, at least one universal primer sequence ranging between four and thirteen nucleotides in length, and at least one random nucleotide sequence of at least eight nucleotides in length;
        iii) a second primer comprising said at least one restriction enzyme binding site sequence;
        iv) a restriction enzyme capable of creating a single nucleotide overhang at said restriction enzyme binding site sequences; and
        v) a polymerase;

b) fragmenting said genomic DNA wherein a plurality of DNA fragments are created;
c) extending said plurality of DNA fragments with said hairpin primer and said polymerase so as to create a first extension product;
d) amplifying said first extension product with said second primer and said polymerase so as to create a second extension product, wherein the 3' and 5' ends of said second extension product each contain said restriction enzyme site sequence;
e) cleaving the 3' and 5' ends of said second extension product at said restriction enzyme sites with said restriction enzyme, thereby creating a 3' cleavage product and a 5' cleavage product wherein each of said cleavage products are identical and comprise said single nucleotide overhang.

2. The method of claim 1, wherein said method further comprises step e) attaching a sequencing adapter to each of said cleavage products via said single nucleotide overhang.

3. The method of claim 1, wherein said genomic DNA fragments are selected from the group consisting of genomic DNA chromatin immunoprecipitated fragments, genomic DNA restriction fragments, and genomic DNA sonication fragments.

4. The method of claim 1, wherein said random nucleotide sequence comprises between approximately eight to eleven nucleotide residues.

5. The method of claim 1, wherein said random nucleotide sequence comprises nine nucleotide residues.

6. The method of claim 1, wherein said polymerase has no 3'→5' exonuclease activity.

7. The method of claim 1, wherein said polymerase comprises strand displacement activity.

* * * * *

SEQUENCE LISTING

<160> NUMBER OF SEQ ID NOS: 54

<210> SEQ ID NO 1
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: The residues in these positions represent a
      common PCR sequence.
<220> FEATURE:
<221> NAME/KEY: misc_feature
<222> LOCATION: (6)..(11)
<223> OTHER INFORMATION: The residues at these positions represent a
      restriction site for BciVI with a location of BciVI restriction
      enzyme cleavage behind residue in position 11.
<220> FEATURE:
<221> NAME/KEY: misc_feature
<222> LOCATION: (12)..(17)
<223> OTHER INFORMATION: The residues in these positions represent a
      common PCR sequence.
<220> FEATURE:
<221> NAME/KEY: misc_feature
<222> LOCATION: (18)..(26)
<223> OTHER INFORMATION: The residues in these positions represent a
      random 9-mer at the 3' end.

<400> SEQUENCE: 1
gacatgtatc cggatgtnnn nnnnnn                                          26

<210> SEQ ID NO 2
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(11)
<223> OTHER INFORMATION: The residues at these positions represent a
      restriction site for BciVI.

<400> SEQUENCE: 2
gacatgtatc cggatgt                                                    17

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tgattgtgag gcgagaactg                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gatcacctgc acaagaacga                                                 20

<210> SEQ ID NO 5

```
<211> LENGTH: 20
<212> TYPE: DNA
<213> ORGANISM: Artificial Sequence
<220> FEATURE:
<223> OTHER INFORMATION: Synthetic

<400> SEQUENCE: 5
caaaggcgga gttaccagag                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ctgcagtact gtggggaggt                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
cagggagttc gcaaaagtct                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tggacatttg attgccatgt                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgggtgtgat gctgtttcat                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ctcagggtcc ttctcactgc                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
```

-continued aacctcacac acaacaagct g                                           21

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
tgtgataggg agaatgcttg c                                           21

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
agagtttgat cctggctcag                                             20

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
acggctacct tgttacgact t                                           21

<210> SEQ ID NO 15
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(13)
<223> OTHER INFORMATION: n is a, c, g, or t

<400> SEQUENCE: 15
gtatccnnnn nnn                                                    13

<210> SEQ ID NO 16
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(13)
<223> OTHER INFORMATION: n is a, c, g, or t

<400> SEQUENCE: 16
cataggnnnn nnn                                                    13

<210> SEQ ID NO 17
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)

-continued

```
<223> OTHER INFORMATION: In some embodiments, the residues in these
      positions may be replaced with T's.
<220> FEATURE:
<221> NAME/KEY: misc_feature
<222> LOCATION: (7)..(7)
<223> OTHER INFORMATION: In some embodiments, the residue in this
      position may be replaced with a T.
<220> FEATURE:
<221> NAME/KEY: misc_feature
<222> LOCATION: (9)..(9)
<223> OTHER INFORMATION: In some embodiments, the residue in this
      position may be replaced with a T.
<220> FEATURE:
<221> NAME/KEY: misc_feature
<222> LOCATION: (17)..(17)
<223> OTHER INFORMATION: In some embodiments, the residue in this
      position may be replaced with a T.
<220> FEATURE:
<221> NAME/KEY: misc_feature
<222> LOCATION: (18)..(26)
<223> OTHER INFORMATION: n is a, c, g, t or u

<400> SEQUENCE: 17
guuccguauc cgaccgunnn nnnnnn                                              26

<210> SEQ ID NO 18
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: In some embodiments, the residue in this
      position may be replaced with a T.
<220> FEATURE:
<221> NAME/KEY: misc_feature
<222> LOCATION: (5)..(5)
<223> OTHER INFORMATION: In some embodiments, the residue in this
      position may be replaced with a T.
<220> FEATURE:
<221> NAME/KEY: misc_feature
<222> LOCATION: (7)..(7)
<223> OTHER INFORMATION: In some embodiments, the residue in this
      position may be replaced with a T.
<220> FEATURE:
<221> NAME/KEY: misc_feature
<222> LOCATION: (9)..(9)
<223> OTHER INFORMATION: In some embodiments, the residue in this
      position may be replaced with a T.
<220> FEATURE:
<221> NAME/KEY: misc_feature
<222> LOCATION: (15)..(15)
<223> OTHER INFORMATION: In some embodiments, the residue in this
      position may be replaced with a T.
<220> FEATURE:
<221> NAME/KEY: misc_feature
<222> LOCATION: (17)..(17)
<223> OTHER INFORMATION: In some embodiments, the residue in this
      position may be replaced with a T.
<220> FEATURE:
<221> NAME/KEY: misc_feature
<222> LOCATION: (18)..(26)
<223> OTHER INFORMATION: n is a, c, g, t or u

<400> SEQUENCE: 18
uccguguauc cggaugunnn nnnnnn                                              26

<210> SEQ ID NO 19
<211> LENGTH: 26
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<222> LOCATION: (1)..(1)
<223> OTHER INFORMATION: In some embodiments, the residue in this
      position may be replaced with a T.
<220> FEATURE:
<221> NAME/KEY: misc_feature
<222> LOCATION: (5)..(5)
<223> OTHER INFORMATION: In some embodiments, the residue in this
      position may be replaced with a T.
<220> FEATURE:
<221> NAME/KEY: misc_feature
<222> LOCATION: (7)..(7)
<223> OTHER INFORMATION: In some embodiments, the residue in this
      position may be replaced with a T.
<220> FEATURE:
<221> NAME/KEY: misc_feature
<222> LOCATION: (9)..(9)
<223> OTHER INFORMATION: In some embodiments, the residue in this
      position may be replaced with a T.
<220> FEATURE:
<221> NAME/KEY: misc_feature
<222> LOCATION: (13)..(13)
<223> OTHER INFORMATION: In some embodiments, the residue in this
      position may be replaced with a T.
<220> FEATURE:
<221> NAME/KEY: misc_feature
<222> LOCATION: (15)..(15)
<223> OTHER INFORMATION: In some embodiments, the residue in this
      position may be replaced with a T.
<220> FEATURE:
<221> NAME/KEY: misc_feature
<222> LOCATION: (17)..(17)
<223> OTHER INFORMATION: In some embodiments, the residue in this
      position may be replaced with a T.
<220> FEATURE:
<221> NAME/KEY: misc_feature
<222> LOCATION: (18)..(26)
<223> OTHER INFORMATION: n is a, c, g, t or u

<400> SEQUENCE: 19
uacauguauc cguaugunnn nnnnnn                                          26

<210> SEQ ID NO 20
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: In some embodiments, the residue in this
      position may be replaced with a T.
<220> FEATURE:
<221> NAME/KEY: misc_feature
<222> LOCATION: (7)..(7)
<223> OTHER INFORMATION: In some embodiments, the residue in this
      position may be replaced with a T.
<220> FEATURE:
<221> NAME/KEY: misc_feature
<222> LOCATION: (9)..(9)
<223> OTHER INFORMATION: In some embodiments, the residue in this
      position may be replaced with a T.
<220> FEATURE:
<221> NAME/KEY: misc_feature
<222> LOCATION: (15)..(15)
<223> OTHER INFORMATION: In some embodiments, the residue in this
      position may be replaced with a T.
<220> FEATURE:
<221> NAME/KEY: misc_feature
<222> LOCATION: (17)..(17)
<223> OTHER INFORMATION: In some embodiments, the residue in this
      position may be replaced with a T.
<220> FEATURE:
<221> NAME/KEY: misc_feature
<222> LOCATION: (18)..(26)
<223> OTHER INFORMATION: n is a, c, g, t or u

```
<400> SEQUENCE: 20
gacauguauc cggaugunnn nnnnnn                                              26

<210> SEQ ID NO 21
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: n is a, c, g, or t

<400> SEQUENCE: 21
actgggnnnn n                                                              11

<210> SEQ ID NO 22
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: n is a, c, g, or t

<400> SEQUENCE: 22
tgacccnnnn n                                                              11

<210> SEQ ID NO 23
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(11)
<223> OTHER INFORMATION: n is a, c, g, or t

<400> SEQUENCE: 23
ccttcnnnnn n                                                              11

<210> SEQ ID NO 24
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(11)
<223> OTHER INFORMATION: n is a, c, g, or t

<400> SEQUENCE: 24
ggaagnnnnn n                                                              11

<210> SEQ ID NO 25
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(11)
<223> OTHER INFORMATION: n is a, c, g, or t
```

<400> SEQUENCE: 25 cctcnnnnn n                                                                                      11

<210> SEQ ID NO 26
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(11)
<223> OTHER INFORMATION: n is a, c, g, or t

<400> SEQUENCE: 26 ggagnnnnn n                                                                                      11

<210> SEQ ID NO 27
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: n is a, c, g, or t

<400> SEQUENCE: 27
gtatccnnnn nn                                                                                    12

<210> SEQ ID NO 28
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: n is a, c, g, or t

<400> SEQUENCE: 28
cataggnnnn nn                                                                                    12

<210> SEQ ID NO 29
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(13)
<223> OTHER INFORMATION: n is a, c, g, or t

<400> SEQUENCE: 29
ggtgannnnn nnn                                                                                   13

<210> SEQ ID NO 30
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: n is a, c, g, or t

```
<400> SEQUENCE: 30
actgggnnnn n                                                          11

<210> SEQ ID NO 31
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: n is a, c, g, or t

<400> SEQUENCE: 31
tgacccnnnn n                                                          11

<210> SEQ ID NO 32
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(9)
<223> OTHER INFORMATION: n is a, c, g, or t

<400> SEQUENCE: 32 actggnnnn                                                              9

<210> SEQ ID NO 33
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(11)
<223> OTHER INFORMATION: n is a, c, g, or t

<400> SEQUENCE: 33
tgacccnnnn n                                                          11

<210> SEQ ID NO 34
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(11)
<223> OTHER INFORMATION: n is a, c, g, or t

<400> SEQUENCE: 34
ccttcnnnnn n                                                          11

<210> SEQ ID NO 35
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(11)
<223> OTHER INFORMATION: n is a, c, g, or t
```

```
<400> SEQUENCE: 35
ggaagnnnnn n                                                               11

<210> SEQ ID NO 36
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: n is a, c, g, or t

<400> SEQUENCE: 36
gtatccnnnn nn                                                              12

<210> SEQ ID NO 37
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(12)
<223> OTHER INFORMATION: n is a, c, g, or t

<400> SEQUENCE: 37
cataggnnnn nn                                                              12

<210> SEQ ID NO 38
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(13)
<223> OTHER INFORMATION: n is a, c, g, or t

<400> SEQUENCE: 38
ggtgannnnn nnn                                                             13

<210> SEQ ID NO 39
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 39 ggatcnnnnn                                                                 10

<210> SEQ ID NO 40
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t
```

```
<400> SEQUENCE: 40 cctagnnnnn                                                                      10

<210> SEQ ID NO 41
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 41 ccatcnnnnn                                                                      10

<210> SEQ ID NO 42
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 42 ggtagnnnnn                                                                      10

<210> SEQ ID NO 43
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 43 gagtcnnnnn                                                                      10

<210> SEQ ID NO 44
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 44 ctcagnnnnn                                                                      10

<210> SEQ ID NO 45
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t
```

```
<400> SEQUENCE: 45 ggatcnnnnn                                                                10

<210> SEQ ID NO 46
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 46 cctagnnnnn                                                                10

<210> SEQ ID NO 47
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 47 ggatcnnnnn                                                                10

<210> SEQ ID NO 48
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 48 cctagnnnnn                                                                10

<210> SEQ ID NO 49
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 49 ggatcnnnnn                                                                10

<210> SEQ ID NO 50
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t
```

```
<400> SEQUENCE: 50 cctagnnnnn                                                              10

<210> SEQ ID NO 51
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 51 gagtcnnnnn                                                              10

<210> SEQ ID NO 52
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: n is a, c, g, or t

<400> SEQUENCE: 52 ctcagnnnnn                                                              10

<210> SEQ ID NO 53
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(18)
<223> OTHER INFORMATION: n is a, c, g, or t

<400> SEQUENCE: 53
acggcnnnnn nnnnnnnn                                                     18

<210> SEQ ID NO 54
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(18)
<223> OTHER INFORMATION: n is a, c, g, or t

<400> SEQUENCE: 54
tgccgnnnnn nnnnnnnn                                                     18
```